(12) United States Patent
Fuerst et al.

(10) Patent No.: US 7,908,155 B2
(45) Date of Patent: Mar. 15, 2011

(54) SYSTEM FOR COLLECTING, STORING, PRESENTING AND ANALYZING IMMUNIZATION DATA HAVING REMOTE STATIONS IN COMMUNICATION WITH A VACCINE AND DISEASE DATABASE OVER A NETWORK

(75) Inventors: Oren Fuerst, New York, NY (US); Zeil Rosenberg, Closter, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 2434 days.

(21) Appl. No.: 10/373,590

(22) Filed: Feb. 26, 2003

(65) Prior Publication Data

US 2011/0029488 A1 Feb. 3, 2011

Related U.S. Application Data

(60) Provisional application No. 60/371,720, filed on Apr. 12, 2002.

(51) Int. Cl.
*G06Q 50/00* (2006.01)
*G06Q 10/00* (2006.01)
(52) U.S. Cl. .............................. 705/3; 705/2
(58) Field of Classification Search .............. 705/2–4; 600/300
See application file for complete search history.

(56) References Cited

U.S. PATENT DOCUMENTS

| | | | |
|---|---|---|---|
| 5,499,293 A | 3/1996 | Behram et al. | 380/4 |
| 5,758,095 A | 5/1998 | Albaum et al. | 395/202 |
| 5,772,585 A | 6/1998 | Lavin et al. | 600/300 |
| 5,899,998 A | 5/1999 | McGauley et al. | 707/104 |
| 5,911,132 A | 6/1999 | Sloane | 705/3 |
| 5,940,802 A | 8/1999 | Hildebrand et al. | 705/3 |
| 5,945,651 A | 8/1999 | Chorosinski et al. | 235/375 |

(Continued)

FOREIGN PATENT DOCUMENTS

FR 2793914 11/2000

(Continued)

OTHER PUBLICATIONS

Macartney, Kristine K., Paul A Offit. How Vaccine Safety is Monitored Before ans After Licensure. Pediatric Annals. Thorofare: Jul. 2001. vol. 30, Iss. 7; p. 392.*

(Continued)

*Primary Examiner* — Robert W Morgan
*Assistant Examiner* — Anita Molina
(74) *Attorney, Agent, or Firm* — Roylance, Abrams, Berdo and Goodman, L.L.P.

(57) ABSTRACT

A system is provided for collecting and storing immunization and disease data. Immunization mobile stations (IMSs) are provided with a software application to facilitate the collection of patient information such as biographical data, previous vaccination data, medical history, medications in use, occupation, administration of recent vaccination, disease symptoms and the like. IMSs synchronize the patient information with information stored in a database maintained at a data center that is accessible to different groups of personnel based on different privileges defined at the data center and security measures. Patients can access electronic patient records created by the IMSs, and stored at the IMSs and/or a local server and eventually at the data center, via telephone or computer (e.g., via web browser). IMSs can capture and store images of vaccination and disease symptom sites on patients. The database allows for vaccination and disease tracking and disease control. The IMSs can be provided with a vaccination recommendation engine to determine if a patient is eligible for a vaccination and electronic patient consent forms, and are programmable to track adverse events and create follow-up reports after a vaccine is administered.

21 Claims, 28 Drawing Sheets

U.S. PATENT DOCUMENTS

| | | | | |
|---|---|---|---|---|
| 6,018,713 | A * | 1/2000 | Coli et al. | 705/2 |
| 6,039,688 | A * | 3/2000 | Douglas et al. | 600/300 |
| 6,047,259 | A * | 4/2000 | Campbell et al. | 705/3 |
| 6,082,776 | A | 7/2000 | Feinberg | 283/72 |
| 6,112,183 | A | 8/2000 | Swanson et al. | |
| 6,148,297 | A | 11/2000 | Swor et al. | 707/3 |
| 6,161,095 | A | 12/2000 | Brown | 705/2 |
| 6,211,789 | B1 | 4/2001 | Oldham et al. | 340/573.3 |
| 6,219,674 | B1 | 4/2001 | Classen | 707/104 |
| 6,238,337 | B1 | 5/2001 | Kambhatla et al. | 600/300 |
| 6,294,999 | B1 * | 9/2001 | Yarin et al. | 340/573.1 |
| 6,347,329 | B1 * | 2/2002 | Evans | 709/202 |
| 6,385,589 | B1 | 5/2002 | Trusheim et al. | 705/2 |
| 6,401,071 | B1 | 6/2002 | Hogan | 705/2 |
| 6,415,295 | B1 | 7/2002 | Feinberg | 707/104.1 |
| 6,523,009 | B1 | 2/2003 | Wilkins | 705/2 |
| 2001/0032099 | A1 * | 10/2001 | Joao | 705/2 |
| 2001/0041991 | A1 | 11/2001 | Segal et al. | 705/3 |
| 2001/0042551 | A1 | 11/2001 | Kutzko et al. | 128/898 |
| 2001/0056228 | A1 * | 12/2001 | Utsugi et al. | 600/300 |
| 2001/0056359 | A1 | 12/2001 | Abreu | 705/3 |
| 2002/0016721 | A1 | 2/2002 | Mason et al. | 705/3 |
| 2002/0029157 | A1 | 3/2002 | Marchosky | 705/3 |
| 2002/0032582 | A1 | 3/2002 | Feeney, Jr. et al. | 705/2 |
| 2002/0038227 | A1 | 3/2002 | Fey et al. | 705/3 |
| 2002/0052759 | A1 | 5/2002 | Cheng | 705/2 |
| 2002/0062225 | A1 | 5/2002 | Siperco | 705/2 |
| 2002/0062228 | A1 | 5/2002 | Portnoy et al. | 705/3 |
| 2002/0072991 | A1 | 6/2002 | Kane | 705/26 |
| 2002/0077851 | A1 | 6/2002 | Cheng | 705/2 |
| 2002/0082868 | A1 | 6/2002 | Pories et al. | 705/3 |
| 2002/0087360 | A1 * | 7/2002 | Pettit | 705/3 |
| 2002/0087362 | A1 | 7/2002 | Cobb et al. | 705/3 |
| 2002/0087437 | A1 | 7/2002 | Hogan | 705/28 |
| 2002/0103675 | A1 | 8/2002 | Vanelli | 705/3 |
| 2002/0128872 | A1 | 9/2002 | Giammattei | 705/3 |
| 2002/0153411 | A1 | 10/2002 | Wan et al. | 235/375 |
| 2002/0161607 | A1 | 10/2002 | Subich | 705/3 |
| 2002/0163435 | A1 | 11/2002 | Kosaka | 340/573.1 |
| 2002/0169638 | A1 | 11/2002 | Rodriquez-Cue | 705/3 |
| 2002/0188468 | A1 | 12/2002 | Hogan | 705/2 |
| 2002/0188470 | A1 | 12/2002 | Hogan | 705/2 |
| 2003/0028399 | A1 | 2/2003 | Davis et al. | 705/2 |
| 2003/0037054 | A1 | 2/2003 | Dutta et al. | 707/100 |
| 2003/0038721 | A1 | 2/2003 | Hogan | 340/573.3 |
| 2003/0055679 | A1 * | 3/2003 | Soll et al. | 705/2 |
| 2003/0135391 | A1 * | 7/2003 | Edmundson et al. | 705/2 |
| 2003/0151506 | A1 * | 8/2003 | Luccketti | 340/539.13 |
| 2004/0006488 | A1 * | 1/2004 | Fitall et al. | 705/2 |

FOREIGN PATENT DOCUMENTS

| | | |
|---|---|---|
| JP | 099589 A | 4/2000 |
| JP | 092895 A | 4/2001 |

OTHER PUBLICATIONS

Immunize.org. Vaccine Administration Record for Children and Teens and Summary of Rules for Childhood Immunization. http://web.archive.org/web/20000817040248/www.immunize.org/catg.d/p2022b.pdf and http://web.archive.org/web/20000817040158/http://www.immunize.org/catg.d/rules1.pdf.*

Feldman, Sandor. Current Smallpox Vaccine Guidelines. Medcape Pediatrics 4(1). Posted Jan. 17, 2002.*

ProQuest Search Jun. 17, 2008.*

Clarke, Sue. "Data Management Research Paper: Object Design Object Store." Technology Infrastructure, Research and Advisory Services. The Butler Group. May 2001. Accessed at http://www.progress.com/realtime/docs/analyst/gated/objectstore60_butler_group.pdf on Jul. 27, 2009.*

Yasnoff et al., "Public health informatics: Improving and transforming public health in the information age. Topics in Health information Management," Feb. 2001, vol. 21, No. 3, p. 44.

Brayden et al., "Efficient vaccination practices. Pediatric Annals," May 2001, vol. 30, No. 5, p. 284.

* cited by examiner

| Find Patient | ☒ |

Find Patient

Search Criteria

First  M  Last

Social Security Number  Vaccination Date  Recent Activity
　　　　　　　　　　　　　　　　　　　　　　　　　　　　minutes 170 — Search

Search Results

View　Cancel

Screening and Immunization

Screening and Immunization - Erez, Rimon.

| Discharge | Take Response | Comments | | | | |
|---|---|---|---|---|---|---|
| Medical History | Current Medications | Immunization History | Approval | Immunization | Photos | |

Medical History

| Question | Patient | Close Contact | Remarks |
|---|---|---|---|
| Allergy to any medications | No | No | |
| Allergy to Streptomycin | No | No | |
| Allergy to Neomycin | No | No | |
| Allergy to Chlortetracycline | No | No | |
| Allergy to Polymixin B | No | No | |
| Allergy to Phenol | No | No | |
| Adverse reaction to smallpox vaccine in the past | No | No | |
| Using meds or inhaler for asthma or emphysema | No | No | |
| Using oral, inhaled or topical steroids | No | No | |
| Taking chemotherapy medications | No | No | |
| Cancer or leukemia | No | No | |
| AIDS or HIV | No | No | |
| Current or past eczema or atopic dermatitis | No | No | |
| Sickle Cell Anemia (not including Sickle Trait) | No | No | |
| Spleen injury or removal | No | No | |
| Organ transplant or taking anti-rejection drugs | No | No | |
| Autoimmune disorder (RA, SLE, Scleroderma) | No | No | |
| Multiple Sclerosis or Vasculitis | No | No | |
| Burns, rashes, open wounds, or herpes (currently active) | No | No | |

Answer Yes or No for each question - Patient and Close Contact

Discharged    Save    Cancel

Screening and Immunization - Erez, Rimon .

Screening and Immunization

| Discharge | Take Response | Comments | | | |
|---|---|---|---|---|---|
| Medical History | Current Medications | Immunization History | Approval | Immunization | Photos |

Current Medications

Current Medications (List all prescription, non-prescription, herbal, oral contraceptive, and fertility medications) ☑ Yes ☐ No

| Medication | Dosage | Start Date | Reason |
|---|---|---|---|
| A-HYDROCORT | EQ 500MG | 12/31/9999 | test |
| * | | | |

Discharged

Save    Cancel

| Follow Up - Erez, Rimon. | | | | | | | | | | | | | | | |
|---|---|---|---|---|---|---|---|---|---|---|---|---|---|---|---|
| *Is selected for editing* | | | 1 | 2 | 3 | 4 | 5 | 6 | 7 | 8 | 9 | 10 | 11 | 12 | 13 | 14 |
| Physical Exam | Comments | Photos | Diary | 15 | 16 | 17 | 18 | 19 | 20 | 21 | 22 | 23 | 24 | 25 | 26 | 27 | 28 |

Follow Up - Day 1

Diary Information

Vaccination Date: 1/1/2001

Skin findings at vaccinia site (Check if present and measure diameter where indicated)

*Temperature (F)  98.6

☐ Redness (around injection site)  0 (mm)  ☐ Scab
☐ Bump/pimple (not fluid filled)  0 (mm)  ☐ Streaks on arm
☐ Vesicle/pustule (fluid filled)  0 (mm)  ☐ Warmth

*Pain  No Pain

Symptoms

| | Category | Yes/No | Description |
|---|---|---|---|
| ▷ | No adverse symptoms | | |
| | Fever | | |
| | Chills | | |
| | Joint pain or swelling | | |
| | Muscle pain | | |

Questions

| | Category | Yes/No | Description |
|---|---|---|---|
| ▷ | Medication for pain or fever (dosage) | | |
| | Vaccinia-type lesion NOT at vaccination site (describe) | | |
| | Vaccinia-type lesion location | | |
| | Non-vaccinia type rash (describe) | | |
| | Non-vaccinia rash location | | |

Save   Cancel

Adverse Event - Erez, Rimon.

Adverse Event

| Event | Comments | Lab results | Vaccinations/Medications | Signature |

Event Information

Vaccination Date 1/1/2001    * Date of onset    * Severity
Lot Number:                    1/1/1950          Mild

* Description of Adverse Event very mild

Details

| Category | Yes/No | Description |
|---|---|---|
| Patient died/date patient died | | |
| Life threatening illness | Yes | test |
| Resulted in significant disability | | |
| Resulted in permanent disability | | |
| Laboratory toxicity | | |
| Assessed as serious by the clinician | | |
| Prolongation of hospitalization | | |
| Required hospitalization and number of days of hospitalization | | |
| Others | | |

Save & Print                          Save        Cancel

| Configuration | ☒ |
|---|---|

Configure Application Settings

| Database | Camera | Vaccine Inventory | Vaccine Batches |

Vaccine and Diluent Inventory

| | Lot # | Received | Manufacturer | Expires |
|---|---|---|---|---|
| ▷ | 2 | 1/1/1900 | ACAM1000 (Acam | 1/1/1900 |
| | 1 | 1/1/2007 | ACAM1000 (Acam | 1/1/1900 |
| * | | | | |

Save  Cancel

FIG. 28

| | Batch | Vaccine | Diluent | Batch |
|---|---|---|---|---|
| ▷ | 1a | 2 | 1 | 1/1/18! |
| | 1b | 2 | 1 | 1/1/20( |
| * | | | | |

FIG. 29

SYSTEM FOR COLLECTING, STORING, PRESENTING AND ANALYZING IMMUNIZATION DATA HAVING REMOTE STATIONS IN COMMUNICATION WITH A VACCINE AND DISEASE DATABASE OVER A NETWORK

This application claims the benefit of U.S. provisional application Ser. No. 60/371,720, filed Apr. 12, 2002.

FIELD OF THE INVENTION

The present invention relates generally to a computer-based information system for conducting, over an electronic network such as the Internet, the transmission of medical information including information pertaining to immunization administrations, adverse events and side effects information records.

BACKGROUND OF THE INVENTION

Immunization Market Overview

The United States immunization industry had over $5 billion in annual revenue in 2000 and is expected to grow at a rate exceeding 10% per year through 2010. The monetary value of the market consists of vaccine delivery devices (around $60 million annually), vaccines (around $2 billion) and vaccine administration (around $3 billion). Additional value derives from lifestyle benefits to consumers (e.g., due to reduced illness), employee productivity gains, and from synergy value to point of care and providers (e.g., enhanced loyalty and the value of new customers for pharmacy chains). The growth potential of the vaccine industry is focused on transferring value from these last two layers to the layers of vaccines and vaccine administration. The factors underlying this expected growth include a large pipeline of preventive and therapeutic vaccines introduced to the market at premium prices.

The immunization market value chain is consistent of various value-added layers. A need exists for a system such as the present invention disclosed below that can address each one of the layers in the immunization market value chain.
Concentrated Manufacturing and Distribution The vaccine manufacturing industry is highly concentrated with more than 75% of the vaccine manufacturing produced by four firms (i.e., Merck & Co., Inc., Glaxo Smithkline, Wyeth Pharmaceuticals SA/NV (formerly AHP Pharma SA/NV) and Aventis Pharmaceuticals Inc.). However, additional firms are increasing their efforts in the area either directly or in collaboration. For example, Baxter is joining efforts with the British company, Acambis plc, in providing the U.S. government with over 150 million doses of smallpox vaccine.

The price of vaccines, such as an influenza vaccine, has been rapidly increasing and is expected to continue to increase in the coming years. That change is due to various Food and Drug Administration (FDA) mandated improvements in manufacturing practice and formulation, which has led to single-dose packaging (i.e., from multi-dose presentation) and increase use of singe-dose pre-filled syringes and other delivery systems. Furthermore, requirements for injection safety and needle-stick protection provide further justification for upward pressures on per dose pricing, and a more attractive environment for vaccine producers. Indeed, despite trends at consolidation elsewhere in this pharmaceutical segment, new players are entering this market (e.g., Baxter Healthcare Corporation, PowderJect Pharmaceuticals Plc) and could benefit from partnering with organization(s) offering the present invention described below.

The market for vaccine delivery tools (i.e., currently standard needles and syringes, safety-engineered syringes to prevent needle-stick injuries, pre-filled syringes and nasal spray devices, and jet injectors) is a highly concentrated market, with Becton, Dickinson and Company (BD) capturing over 70% of the market. The distribution of vaccines is also concentrated, and the top three distributors (i.e., Mckesson Corporation, Cardinal Health Inc., and Bergen Brunswig Corp.) are capturing more than 85% of the market, and suffering from reduced margins as a result of pricing pressures.

A need exists for a system such as the present invention described below that can assist the participants in this layer by offering tools to assist them when incorporating information from the immunization process into their supply chain management system.
Fragmented Vaccine Administration (Providers and Points of Service)

The healthcare delivery industry in the United States is highly fragmented and lacks consistent quality of service. In particular, the immunization market has characteristics that lend itself to centralized information systems (such as centralized registry and recommendation systems) and immunization programs management systems (e.g., the service does not require on-site medical doctors, but rather standing orders issued by a physician medical director for qualified nurses providers). The healthcare delivery industry therefore remains highly inefficient in the manner in which it records and analyzes information, and in the way it ensures consistent and high quality immunization administration service.

Most immunizations are administered today at one of three types of locations, that is, physicians' offices, community clinics and medical center outpatient departments, which together are responsible for over 80% of the market. However, the vaccine administration market is highly fragmented, with no single administrative organization, or point of service network responsible for more than 5% of the market.

Immunization itself does not require medical doctors on the premises for supervision, and therefore is feasible in settings out of health clinics, that is, so called "non-traditional" settings. In recognition of the importance of such settings for accelerating immunization coverage, new guidelines have been issued by the Center for Disease Control (CDC) in 2001 to further enhance their use. Market research indicates that most people, particularly adults, will find locations such as drug stores or worksites to be more convenient for receiving immunization than health clinics. Part of the key to success of an organization offering a service such as the present invention described below is the ability to leverage this consumer inclination to facilitate offerings at national drug store chains (60,000 locations in the U.S.) and at worksites, providing increased convenience to consumers, and enhanced compliance monitoring for employers.

On the provider side, nurse aggregation organizations, usually isolated, could join a certified providers network and benefit from being associated with a high quality brand and become eligible to service referrals to clients previously unobtainable. An organization managing a service such as the present invention described below could also allow for national plans to be coordinated for retail chains and multi-location employers, whereby different providers belonging to the network will provide the immunization service at different locations with a standardized quality, cost and information platform while reducing large risks and costs inherent in managing such an effort independently.

Immunization Information Systems

Information systems play a significant role in healthcare, but currently, they are not utilized in an efficient or useful manner in the immunization market. For example, there is currently no national registry system for the tracking of immunization of adults or children. However, in the last 7 years, more than $250 million has been spent, by government and state agencies, on state pediatric registry systems. Many of these systems are now defunct due to state-based contracting with small software companies that went bankrupt. The present invention described below provides a platform that is superior to any available system by being designed to offer a national private sector registry as part of the benefits of utilizing its services. This registry will be available to children, adolescence and adults. The CDC has an initiative (termed "Vaccine Identification Standards Initiative" or VISI) to provide machine-readable tracking information on vaccines. This initiative, although supported by the major vaccine companies, has not yet been implemented. Such tracking has begun in Europe and is required in some countries there, and this trend is expected to continue. Such vaccine identification system could be combined with input units such as barcode readers connected to a mobile unit of the present invention. This vaccine safety enhancement tool will provide another benefit for medical providers such as hospitals and clinics implementing the system because this component of vaccine administration is the largest nursing dis-satisfier in immunization programs. Moreover, vaccine manufacturers desire that such information be collected both as a method of improving vaccine supply chain efficiency and re-distribution, as a value-added feature to position higher value vaccine packaging and pricing, and as a desired epidemiological tool to more expeditiously conduct investigations of adverse events and avoid larger product recalls than needed.

Bio-Warfare Preparedness

In recent years, attention to national preparedness for bio-warfare scenarios has increased. However, resource allocation in that area had been limited, and was focused instead on disease surveillance by specialists, and not on development of an infrastructure for mass and rapid vaccine delivery capabilities at community levels for emergency situations such as smallpox, anthrax, or influenza pandemic disease occurrences.

Immunization against infectious diseases is a recognized and heavily funded, critical component of national bio-terrorism preparedness and armed forces defense. The market has naturally segmented itself into two distinct portions concerned with likely bio-agent threats, that is, (a) deployment of existing vaccines to military and civilian populations, and (b) the accelerated development of new vaccines to counter likely bio-terror agents. The most significant and immediate priority is immunological defense against smallpox. This infectious disease had been eradicated in 1978, following a global immunization campaign, but has reportedly been weaponized by the former Soviet Union and may also be available as a weapon of mass destruction in Iraq, Syria, Iran and North Yemen, among others. Indeed, as the anthrax exposures in October 2001 have clearly indicated, even a single re-introduction of this disease could create a national and international health crisis.

Various simulations and live-scenario analyses (including the widely reported "Dark Winter" exercise) have indicated that without full and rapid response, smallpox spread undetected and uncontrolled could rapidly result in millions of deaths and disruption of service across a nation. For these and other reasons, the United States government has recognized smallpox to be its primary bio-threat for which mass immunization could be deployed.

Intense public and high-level policy debate is beginning on which strategies will be used for smallpox vaccination preparedness. As of January 2002, the U.S. government has different immunization plans according to the specific needs of each group: (1) pre-event immunization for military and reserve forces; (2) pre-event immunization for family members of military and reserve forces (3) pre-event immunization for core first responders (4) pre-event immunization for all first responders (5) post event, rapid immunization (<3 days) for designated populations (6) post event, rapid (<3 days) immunization for all populations. Regardless of the combinations and evolution of strategies, the system of the present invention described below can accommodate all these strategies using ongoing direct involvement at the public health policy levels.

SUMMARY OF THE INVENTION

In accordance with the present invention, an immunization data system comprises single or multiple networked mobile (e.g., portable) or stationary units, connected directly or via a local server to a centralized data-center. The system provides management and referral tools for point of care managers such as states, worksites, pharmacies and retail stores interested in solutions for immunization and bio-warfare preparedness services, information tools such as lifetime vaccination tracking, and a vaccination recommendation engine to address the needs of consumers and employers.

The immunization data system collects and stores immunization and disease data. The networked mobile (e.g., portable) or stationary units (hereinafter referred to as "immunization mobile stations" or IMSs) are provided with a software application to facilitate the collection of patient information such as biographical data, previous vaccination data, medical history, medications in use, occupation, administration of recent vaccination, disease symptoms and the like. IMSs synchronize the patient information with information stored in a database maintained at a data center that is accessible to different groups of personnel based on different privileges defined at the data center and other security measures. Patients can access electronic patient records created by the IMSs, and stored at the IMSs and/or a local server and eventually at the data center, via telephone or computer (e.g., via web browser). IMSs can capture and store images of vaccination and disease symptom sites on patients. The database allows for vaccination and disease tracking and disease control. The IMSs can be provided with electronic patient consent forms, and are programmable to track adverse events and create follow-up reports after a vaccine is administered.

In accordance with an embodiment of the present invention, a method of collecting and storing immunization data for a patient is provided that comprises the steps of: (1) running an application on a computer at a vaccination site for entering patient information selected from the group consisting of name, age, gender, address, medical history, medications in use by the patient, occupation, and previous vaccination data; (2) storing the patient information as an electronic patient record; (3) generating information relating to a vaccination for review by the patient; (4) obtaining patient consent to receive the vaccination by generating an electronic consent agreement and storing the patient's digital signature acknowledging acceptance; and (5) entering new vaccination data relating to the vaccination into the electronic patient record when the vaccination is administered to the patient.

In accordance with another aspect of the present invention, the method further comprises the steps of generating a digital image of a vaccination site on the patient, and storing the digital image in the electronic patient record. In addition, disease information comprising symptoms (e.g., for smallpox) experienced by the patient can be entered and stored in the electronic patient record. The EMSs are configured to generate a digital image of a smallpox lesion site on a patient, and store the digital image in the electronic patient record.

In accordance with yet another aspect of the present invention, the disease information in the database is accessible by personnel selected from the groups consisting of a disease control center, a state government office, a federal government office, a medical center. Also, a patient can access the electronic patient record using at least one of a web browser and a telephone transaction.

The system of the present invention is configured to collect and store adverse effects information comprising symptoms experienced by any of the plurality of patients following their vaccination in the corresponding the electronic patient record.

BRIEF DESCRIPTION OF THE DRAWINGS

The various aspects, advantages and novel features of the present invention will be more readily comprehended from the following detailed description when read in conjunction with the appended drawings, in which:

FIGS. 7 through 29 are exemplary screens generated by an immunization mobile station or at a data center in accordance with an embodiment of the present invention.

Throughout the drawing figures, the reference numerals will be understood to refer to like parts and components.

DETAILED DESCRIPTION OF THE PREFERRED EMBODIMENTS

Figure 1:
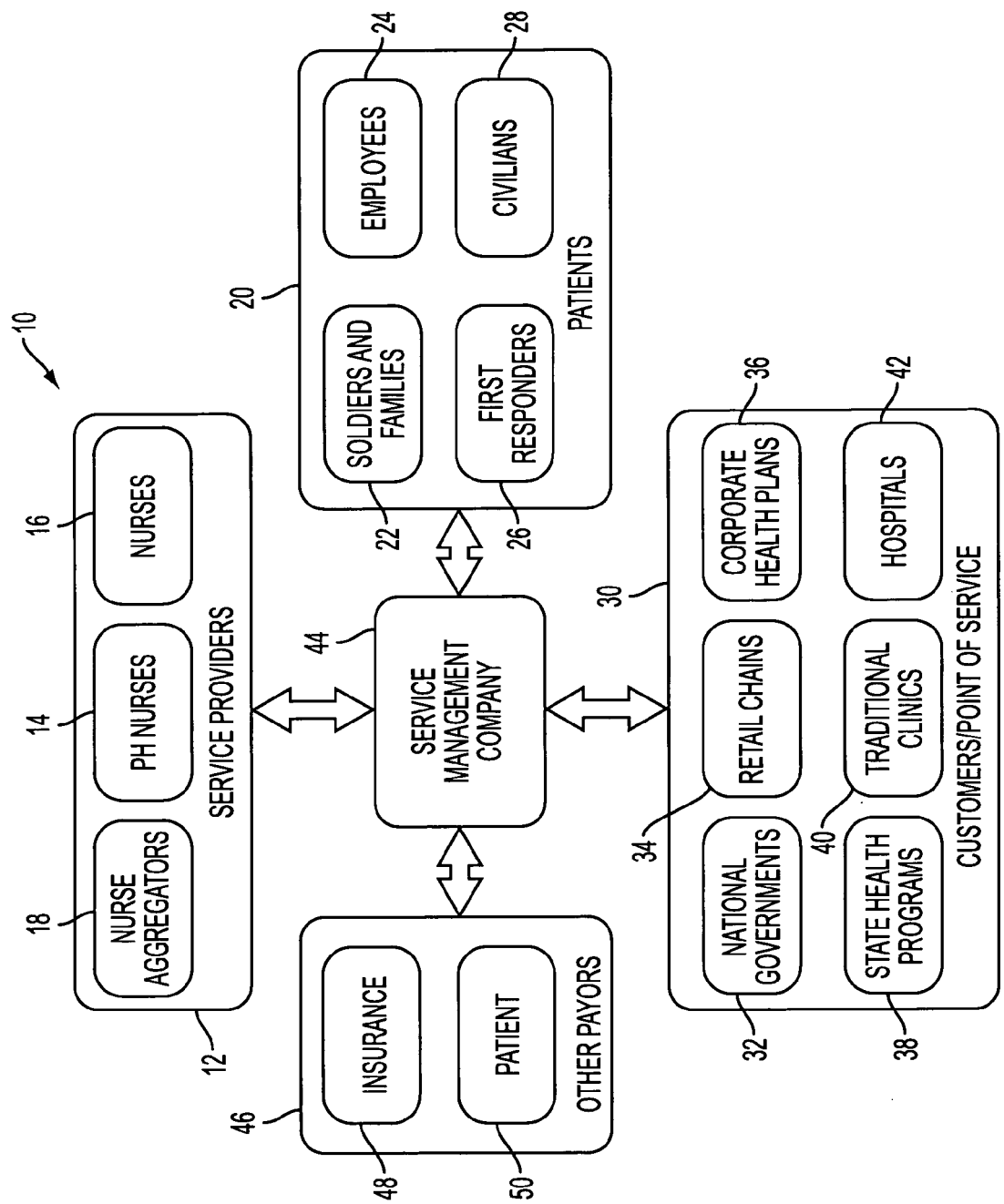
FIG. 1 is a system block diagram illustrating a business process according to an exemplary embodiment of the present invention.

FIG. 1 is a block diagram illustrating a business process employed by an immunization data system 10, according to the present invention. Transactions within the immunization data system 10 can involve service providers 12, patients 20, customers or points of service (POSs) 30, a service management company 44 and payors 46 for services. The service providers 12 can include, but are not limited to, personnel that administer vaccinations such as public health (PH) nurses 14 and private sector nurses 16, as well as nurse or other health professional aggregators 18. The patients that receive vaccines, have adverse reactions to vaccines, exhibit disease symptoms, or otherwise desire access to a database of disease and immunization data can include, but are not limited to, soldiers and their families 22, employees 24, first responders 26 to an emergency such as a bio-terrorism attack, and civilians 28. Customers and POSs that need access to, as well as collect the data for, the database of disease and immunization data can include, but are not limited to, national government facilities 32, retailers (e.g., drug stores) 34, corporate health care administrators 36, state health program facilities and administrators 38, health clinics and offices 40 and hospitals 42. A service management company 44 is preferably any entity that provides an interface between any of service providers 12, patients 20, customers or points of service (POSs) 30, and payors 46 for services. The payors 46 can include, but are not limited to, insurance companies 48 and the patient 50.

As described below in connection with FIG. 2, the system 10 is preferably a combination of computer hardware and software tools designed to enable an immunization program to be conducted in multiple environments. For example, for emergency bio-terror activities, the system 10 allows for a state or other government entity to license a system and incorporate it into its preparedness plan to have a paperless process in place for tasks such as immunization administration, case finding and adverse events follow-ups. The providers 12 of the services in this case will typically be public health (PH) nurses 14 and private sector nurses 16.

Another illustration of the applicability of the system 10 is for routine immunizations at worksites. The manager of the system 10 provides a matching service between the immunization providers using the standardized system and the corporations desiring the service.

Utilizing the system 10 offers various participants in the immunization market significant benefits. For example, benefits to consumers or patients 20 and providers 12 can include, but are not limited to: (1) providing consumers with objective information, support and updates regarding immunization; (2) providing personalized health information while adhering to the strictest confidentiality standards, with the advantage of personal health information handled by the private sector, as opposed to state or government agencies (as it is the case with the pediatric registries); and (3) providing valuable, credentialing for nurses.

Benefits to customers and points of service 30 can include, but are not limited to: (1) a tracking system that allows for updated information, and for annual reminders, supporting achievement of high immunization coverage for high risk and other targeted patient groups at low cost (e.g., such coverage is often viewed as an important indicator of service quality by third party payors, consumers and other agencies); (2) a tracking system that provides an effective tool for loyalty enhancement; (3) allowing pharmacies, retailers, worksites and governments to benefit from a standardized technology platforms and work processes for the management of immunization programs; (4) and a tracking system that offers a simple tool to provide otherwise burdensome information to patients, and provides a simple, low cost employer solution to monitor compliance with regulatory requirements.

Benefits to health programs 38, in particular, state health programs can include, but are not limited to: (1) significant cost saving and rapid implementation through a standardized, modular approach; (2) highly scalable design leveraging existing technologies to expedite development and reduce costs; and (3) meeting emergency preparedness needs while strengthening routine disease control and immunization programs.

Figure 2:
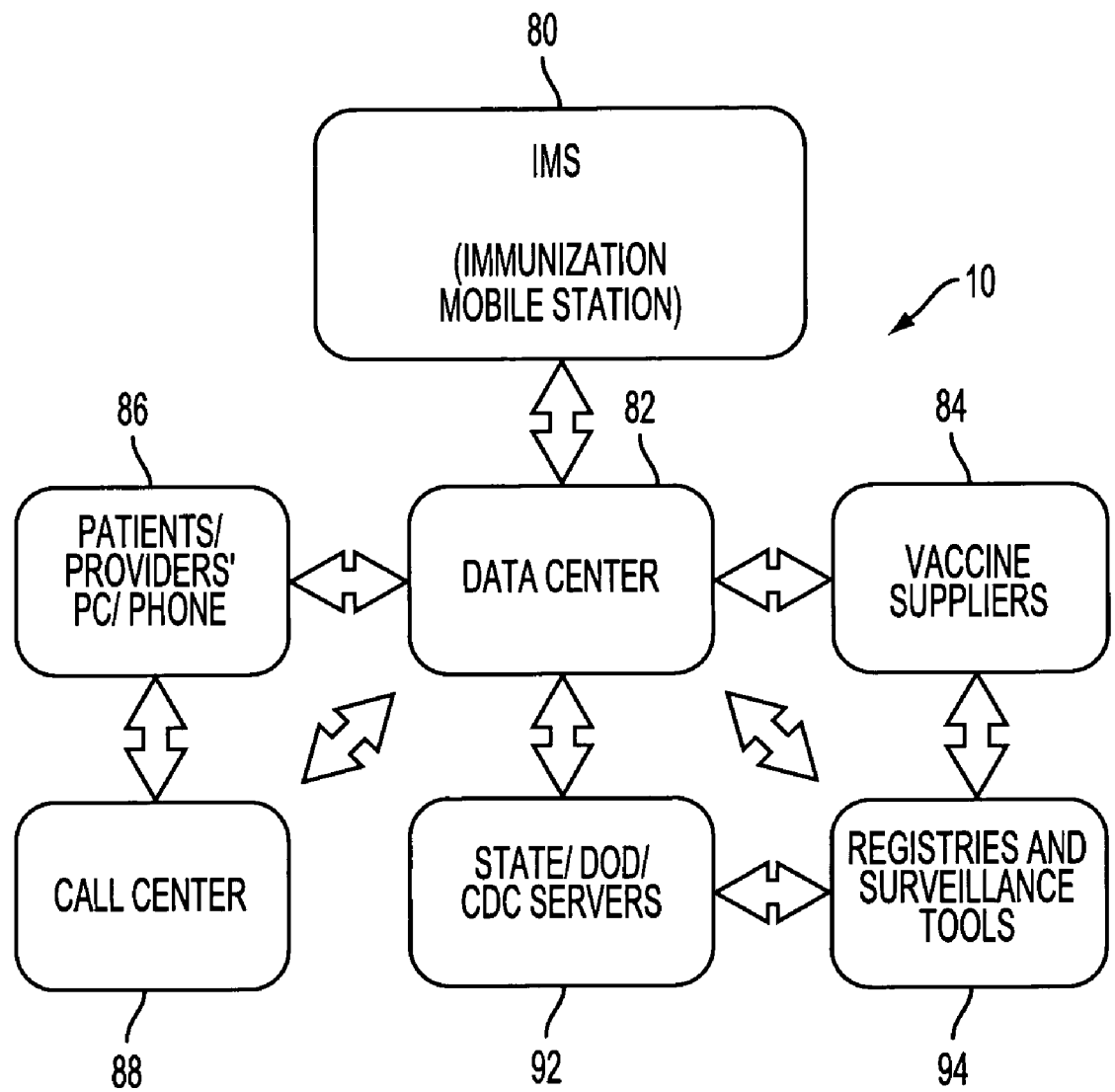
FIG. 2 is a system block diagram of an immunization data system constructed according to an exemplary embodiment of the present invention.

FIG. 2 illustrates the block diagram of the immunization data system 10 according to an embodiment of the present invention. The system 10 preferably comprises at least one data center 82 for storing immunization data collected by one or more immunization mobile stations (IMSs) 80, among other data. As will be described below in connection with FIG. 3, the IMSs 30 are generally located remotely with respect to the data center 82. The data center 82 is accessible by vaccine suppliers' computer systems, as well as by patients and providers, indicated generally at 86, directly or indirectly via a call center 88. Registries and surveillance tools 94 can access and use the data center 82 directly or indirectly via, for example, servers 92 maintained by states, and government agencies such as the Department of Defense (DOD) and Center for Disease Control.

The immunization data system 10 can be implemented by hardware and software components specifically designated to implement the present invention, or by using hardware and software components and other infrastructure that already exists. As an example, an immunization mobile station (IMS) 80 can be connected to the data center 82 via Internet connections, closed circuit connections, or direct lines. The computer system for the IMS can be specially designed computers, or existing computers and technologies such as the preferred embodiment utilizing mobile computers such as a Tablet or Pocket personal computer (PC).

Figure 3:
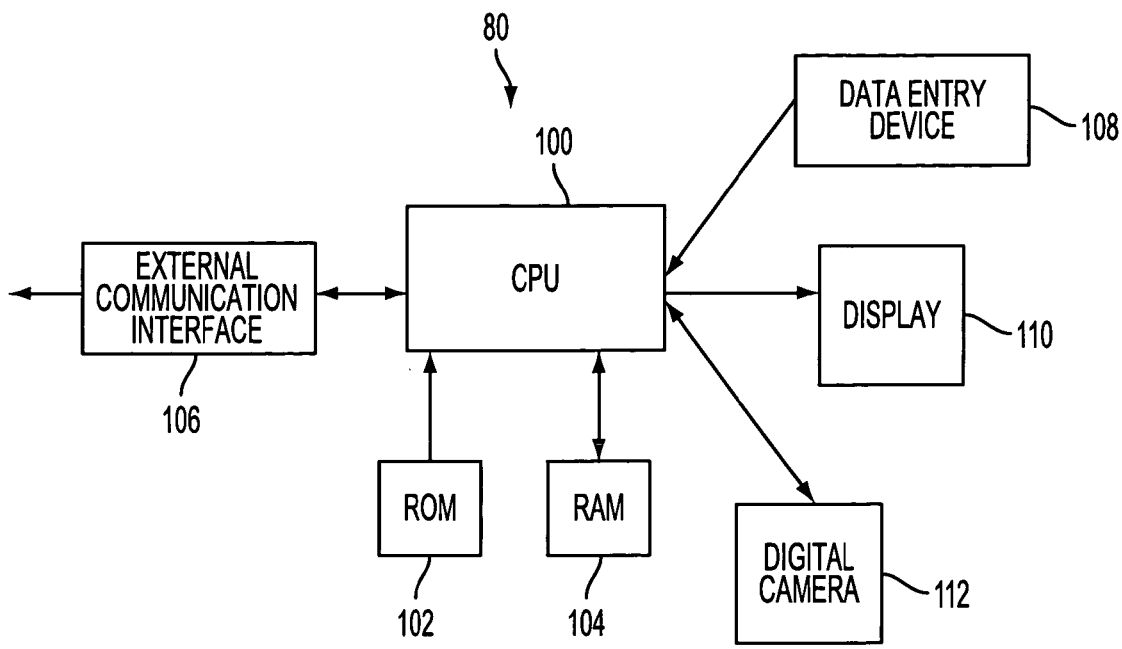
FIG. 3 is a block diagram of an exemplary immunization mobile station constructed in accordance with an embodiment of the present invention.

With reference to FIG. 3, the IMS 80, which is primarily used for data entry, comprises a central processing unit (CPU) 100 for performing processing functions, a Read Only Memory (ROM) 102 and a Random Access Memory (RAM) 104. The ROM 102 stores at least some of the program instructions that are to be executed by the CPU 100, and the RAM 104 provides for temporary storage of patent, immunization and disease data. The term CPU, as generally used herein, refers to any logic processing unit, such as on or more microprocessors, application-specific integrated circuits (ASIC), and the like. While the CPU is described separated from other components such as the ROM, some or all of these components may be monolithically integrated onto a single chip.

A communication port or other interface 106 in the IMS 80 facilitates communication between the CPU 100 and devices external to the IMS. Information between CPU and remote locations such as the data center 82 and a seller computer system can be sent via modem, for example. The illustrative embodiment described herein employs a modem and a wireline link to communicate with devices outside the buyer/seller computer system; however, other paths and methods of communicating with external devices can be used without departing from the spirit of the invention, including, but not limited to, wireless communications and optical communications.

The IMS 80 computer system also includes one or more input/output (I/O) devices such as a display 110 and a data entry device 108 for use by the patient and the medical provider, for example. A wide variety of I/O devices can be implemented for this task, including, but not limited to, a touch screen, a keyboard and a mouse. The I/O device 108 may be linked to the CPU directly or via an intermediate or wireless connection such as an infrared link. In accordance with an aspect of the present invention described in more detail below, the IMS 80 is preferably configured to receive and store images obtained, for example, via a digital camera 112. The IMS 80 is therefore configured to collect and store patient data such as images of a patient's smallpox lesions for better disease monitoring, study and control.

The information entered via the IMS 80 is transmitted to the data center 82 for storage and analysis, or is stored and analyzed by a software program located on a local computer system described below in connection with FIG. 5. The immunization data system 10 of the present invention supports all of the relevant tasks associated with providing high quality immunization delivery service. Among other tasks, the system 10 provides information on dosing schedules for vaccines, supports point of service data entry, provides manufacturers with complete lot tracking, provides consumers with immunization lifetime tracking, contains an immunization recommendation engine based on previous vaccination, demographic, travel, health risk, occupational status and other voluntary information inputs, and provides up-to-date, accurate, on-demand information about vaccines, based on information from an independent panel of expert clinicians.

Main Data Center

Figure 4:
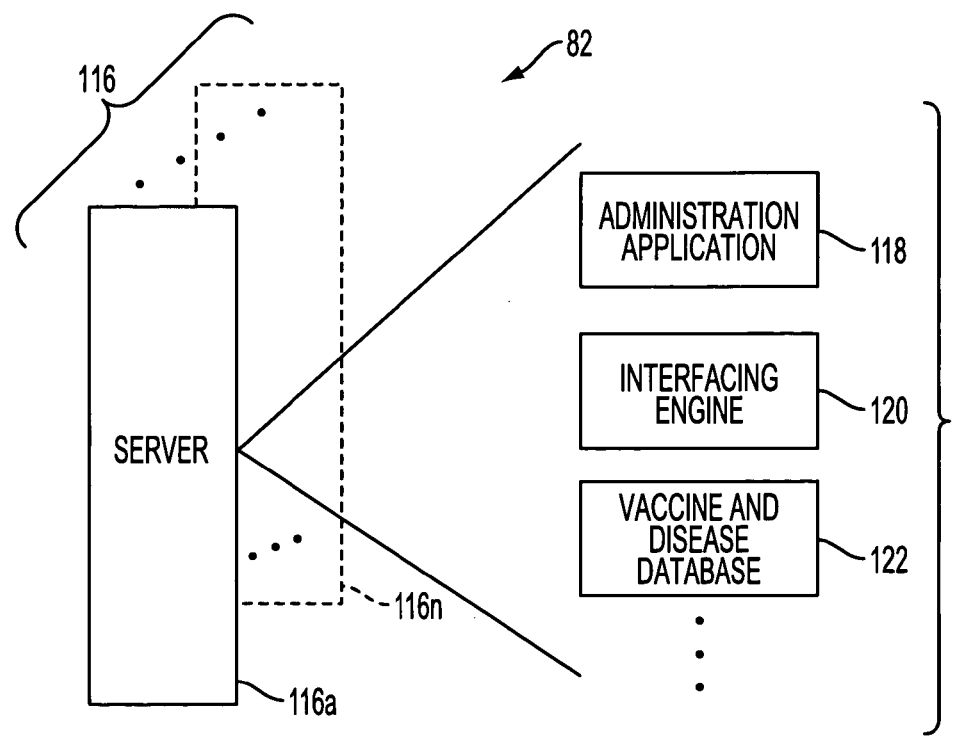
FIG. 4 is a block diagram of an exemplary data center constructed in accordance with an embodiment of the present invention.

With reference to FIG. 4, the main data center 82 preferably resides on a main server 116 and employs an administrator application 118 to configure the IMSs 80 or other software used at the points of service 30. Access rights, database analysis tools, and the rules, procedures and methodologies are preferably defined for all users at the main data center 82. Similarly, the definition of point of service level security privilege is conducted at the data center 82. An interfacing engine 120 allows the import and export of data from and to other information systems, including surveillance systems, state registries, billing companies, and data systems of the points of service.

At the data center 82, a vaccine preventable disease database 122 preferably resides to provide caregivers and consumers with information related to vaccine preventable infectious diseases and the ability to check sequence vaccine administration. The database 122 also allows access to data on risk-based exemptions to prevent adverse events and provides context-based vaccine recommendations (e.g., vaccination recommendation for business travel and personal health promotion).

Immunization Mobile Station (IMS)

The IMS 80 is a combination of applications residing on mobile units such as a standard Tablet PC or a Pocket PC. In the case of a Tablet PC, peer-to peer data sharing is available across units in a pre-defined proximity, even when a wide area network (WAN) is not available, providing the ability to conduct multi-unit immunization in the field without interne or LAN connectivity. The IMSs 80 are essential tools in providing the ability to have a paperless immunization process anywhere, anytime using traditional and non-traditional channels (e.g., schools and worksites). In addition, the IMSs 80 are configured so that some information is always being retained on the unit in the event the Internet or other connection is lost for a period of time.

The IMSs 80 are used for interfacing with patients at the points of service 30, and include immunization administration tools. The applications available on each IMS 80 include, but are not limited to:

Intake patient information: (e.g. name, address, age);
Previous available immunization information, if not otherwise in the system;
Recommendation engine with suggested vaccinations due and next recommended visit date;
Vaccine Information Statements (VIS); and
Informed Consent with electronic signature capability; FAQs to answer questions about the vaccine schedule, contraindications and/or recommendations.

For the case of a bio-terror immunization program, specialized modules can be incorporated into the IMS 80 with the following core and optional enhanced features, for example:

Investigational New Drug consent, monitoring and tracking forms to allow for automated compliance with CDC and NIH extensive mandated protocols for adverse events and side effects documentation; and Global positioning/mapping software to allow for simplified case investigation, contact tracing and analysis of both epidemic spread and control efforts with web-based real-time analysis (for ring containment, this essential tool facilitates coordinated quarantine, tracing and immunization to highest risk individuals in the field or at fixed site immunization stations).

The IMS 80 preferably provides a health management tool that gives patients the ability to build a permanent electronic immunization record in which health information can be collected at the IMS 80 and securely stored (e.g., at the data center 82) as it accrues over time. The data center 82 is accessible by patients and providers with access-rights via computer or telephone. Security for input and retrieval of data allows records to be accessed, with patient permission, to satisfy various periodic vaccine documentation needs from schools, camps, tours, employers and others who require such information. For example, for smallpox immunization, the record could include follow-up tracking information and adverse events follow-up information, including digital images of the lesions requiring expert assessment and notification to state authorities.

The immunization data system 10 can be implemented in many different settings. For example, by way of illustration, three methods of connecting the IMSs 80 to the data center 82 are described. There are several ways in which the IMS 80 can connect to remote networks (e.g., in the field with other IMSs 80) or to the main network 82 (e.g., in a clinic, etc). The IMS can be installed on a standard mobile computer, such as a Tablet PC. Through built-in wireless support (e.g., wireless network cards), Tablet PC's can communicate directly with one another in the field by forming "ad-hoc" networks and exchanging information over their wireless cards. In each group of Tablets PCs, one of the units is designated the group master and retains all updated information regarding the group. In environments where the main network is accessible, the Tablet PCs 80 can be connected to the data center 82 by using their wireless connection to communicate with a wireless access point (WAP), or by utilizing a docking station which is already connected to the main network that connects the IMSs 80 to the data center 82. However, in order to retain the ability to work without internet connectivity, group master units 80 preferably retain all updated group information. All wireless communications between Tablet PC devices 80 and/or WAP devices can be encrypted to ensure secure data transmission. As an alternative to the peer-to-peer communication described above, another notebook computer can operate as a local server.

Figure 5:
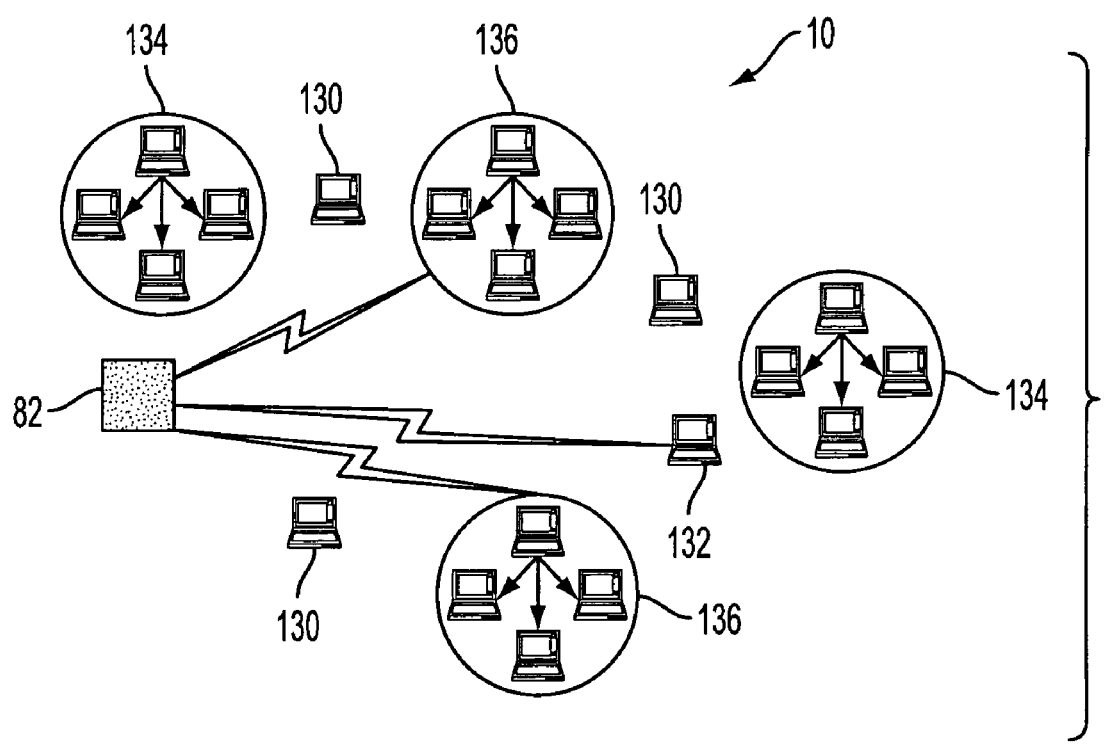
FIG. 5 is a block diagram illustrating different configurations for connecting an exemplary immunization station to a data center in accordance with an embodiment of the present invention.

FIG. 5 illustrates different possible working modes. The IMSs 80 (e.g., Tablet PCs) indicated at 130 represent units working in stand-alone mode, capturing all of the data on the unit 80. The IMSs 134 can also have connection to the data center 82 and synchronize the information with it once they have connectivity, as indicated at 132.

The IMSs 80 indicated at 134 are operating in a Group Mode, where one Tablet PC (e.g., or a regular PC) operates as a group master for a group of IMSs 80 at, for example, a clinic or other site with multiple stations. Information regarding patients belonging to the group is preferably always maintained at the group master, even when there is an Internet connection to the data center 82, as indicated at 136.

During the period when there is connectivity with the data center 82 and the system 10 is operating in the Global Mode, the data is periodically synchronized to maintain consistency between the data center 82 and the group master. In order to switch back to a group mode or global mode, the data stored locally is transferred and synchronized to the master unit, or to the data center 82, correspondingly.

Figure 6:
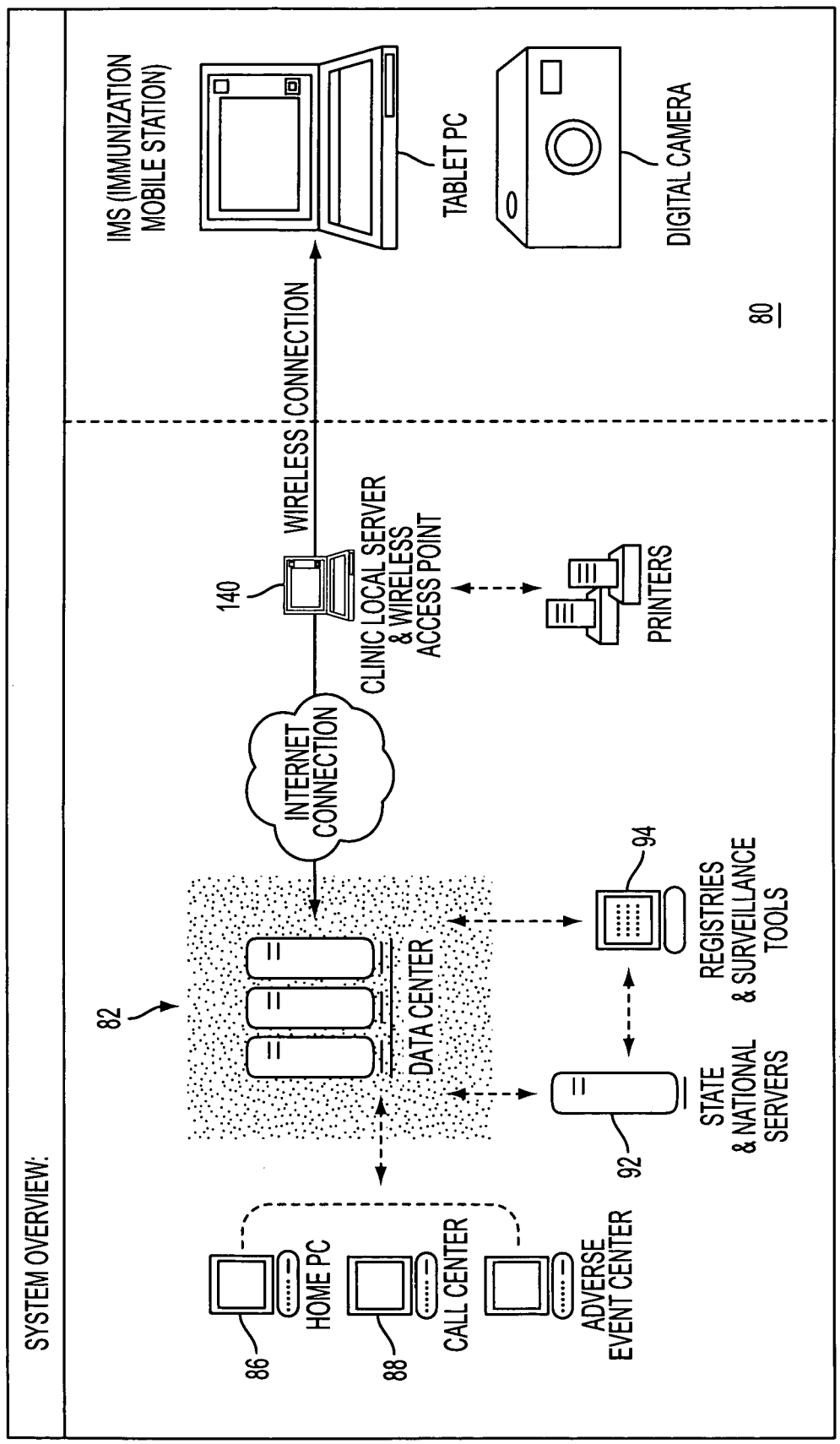
FIG. 6 illustrates an immunization data system constructed in accordance with the present invention comprising an immunization station, a local server and a data center.

FIG. 6 provides an overview of a system whereby an IMS 80 is part of a networked immunization process solution. While the description corresponds to a smallpox immunization process, the methodology can be easily applied to other types of immunization.

The methodology uses a data center 82 where preferably the entire database is retained and backed-up on multiple servers. The data center 82 is preferably connected via the Internet to mobile clinics. Data from local mobile servers 140 are replicated to the data center when an internet connection is available and connection to the data center is initiated. Each mobile clinic is (e.g., IMS 80) based on a local mobile server 140 (e.g., a notebook computer) where the clinic data is replicated, a wireless access point and a printer, as well as a number of IMSs 80. Each IMS 80 (e.g., a Tablet PC and a digital camera) is designed to communicate with the local server 140 using a wireless connection, and directly with the data center 82. The digital cameras can be used to document the patient and skin lesions and, subject to state policies and privacy compliance programs, the resulting patient data set can be designed to be accessible remotely by state designated officials. State designated officials can have access to the entire information residing at the data center 82.

Forms and procedures are provided by each IMS 80 to add a new patient record or to pull an existing patient record. Each IMS 80 can also a personal information page, an informed consent form (with digital signature), a medical history questionnaire (including current medications), a summary page, a smallpox immunization record screen, follow up (diary card) screens, an adverse events screen, among other forms and screens. The screens can be filled via the IMSs 80, which are based on configured Tablet PCs, which allow for signing on the screen. The IMS 80 also allows for the printing of various forms, such as the patient card (which describes details such as the date of vaccination), and the CDC Vaccine Adverse Event Report (VAERS). Summary information regarding the number of patients that visited the clinic can be obtained from the data center, via the internet, using standard browsers, such as Microsoft Internet Explorer. The IMS application environments will now be described.

Exemplary Clinic/Pod Equipment Layout

Each clinic preferably comprises a stationary master tablet PC or another notebook computer 80 and a few other Tablet PCs 80 that are most likely portable devices. The master PC acts as a local database server and as an additional unit in the clinic to run reports and access patients' files. For example, if the clinic manager needs to run a report, he will be able to do this using the master PC without interfering in the operations of other staff members or their respective IMSs 80. Having one extra Tablet PC in each clinic that is stationary ensures reliability of the application at a low cost and prevents malfunctions that can occur if it were a portable unit.

Data Services Tier

Each local IMS 80 could use a standard database client such as Microsoft SQL Server 2000 Desktop Edition (MSDE), a low cost database engine which provides SQL Server compatibility. The data center 82 preferably uses a standard database such as a Microsoft SQL Server 2000.

Security

Application

Access to the IMS 80 application is preferably controlled through a username and password login. Administration of the accounts are preferably handled by senior Help Desk personnel.

Network

With continued reference to FIG. 6, network communication between Tablet PCs 80 and wireless access points indicated generally at 140 in each clinic or other site can be secured using standard security measures, such as 128-bit wired equivalent privacy (WEP) encryption protocol. In addition, other security measures can be used such as data packages transmitted between Tablet PCs 80 and access points 140, or other Tablet PCs can be encrypted using IPSec protocol. Network communication to the data center 82 servers 82 are preferably over the Internet using HTTPS protocol.

Physical

Placing the central database servers in a hosted data center environment 82 provides the best physical security. Access to the servers is preferably controlled by key card access and sign in via security personnel. Hosting providers can also provide network security through use of firewalls, monitoring, and encryption technologies.

Database Security

The database resides behind a firewall that enables access only to authorized users.

Application Layout

General Rules

The application at each IMS 80 preferably follows a set of rules such as the exemplary rules described below that are preferably applicable throughout the entire application screens and forms.

System Login

Each user has a username and password, and has to provide this information in order to access the application.

Patient File Audit Trail

The application creates a log item when a patient's records are created or updated. In each area of the application, the user has the ability to view the patient's log. The system preferably automatically records (without involving the user) the following information:

Patient name
Date
Time
User Name
General activity described in terms of application area used
Date Fields Date fields are text box fields with a date icon next to them. The user can either fill in the field by typing the date or by clicking a date icon that opens a calendar and allows him/her to go back and forward in increments of months and years. Clicking on a specific date in the calendar closes the calendar and displays the selected date in the date text box.

Numeric Values

In numeric fields, the IMS application allows only numeric values. No alphabetic values are allowed in these fields. In addition, for each field, there is a valid range that are defined in the system tables. If the value entered is above or below this range, the system displays an error message. For example, the system does not allow entry of a value such as 150 in the temperature field.

Grids

Each table in the system that displays information can be sorted. The sorting fields are the table headers. The sorting is done by double clicking on the header field the user wishes to sort by. The first time the user double clicks on the grid, the IMS application sorts the data in ascending order. The second time the user double clicks the grid header, the IMS application sorts the data in descending order. The application can sort both numeric and alphabetic values.

The decision to use a grid or not to display a list of questions is a user interface decision that is made on a case-by-case basis to ensure the best accessibility and usability for each portion of the application.

As a general rule, and unless otherwise specified, a tab with five additional positions for questions is preferably provided in each of the sections containing questions. These questions are not required or predetermined by the application. The user enters both the question and the answer. The questions are labeled plainly (e.g., Q1-5). Each question has three available fields labeled:

Question—Text box
Yes/No—Checkbox
Details—Textbox

Application Container Window

The IMS 80 application is preferably a Windows application. A screen can comprise one or more of a top frame, an action form and a bottom status bar, as described below.

Top Frame Menu Items

The top frame contains high-level menu items. Clicking on any of the following menu items opens a new window inside the application. The items are divided into logical areas that support the vaccination process in the clinic or at the field. The availability of items in the top frame menu depends on the status of the vaccination process of the individual patient. For example, the user will not be able to click on the Enrollment item before completing the Consent form. The rules for the menu items will now be discussed.

Search/Open

Clicking the Search/Open menu item 156 displays the search form (FIG. 8) that allows the user to search for existing users in the immunization data system 10.

New Patient

Clicking the New Patient menu item 158 displays a new patient form that allows the user of the IMS 80 to enter new patient information.

Consent

Clicking a Consent menu item (not shown) or completing a new patient form, displays a Consent form that allows the patient to read and sign on a consent form.

Enrollment and Vaccination

Clicking an Enrollment or Patient Information menu item 160 displays an enrollment form that allows the user of an IMS 80 to enter medical information about the patient and his family, record vaccination information, take pictures and have the patient sign after the vaccination process.

Follow Up

Figure 7:
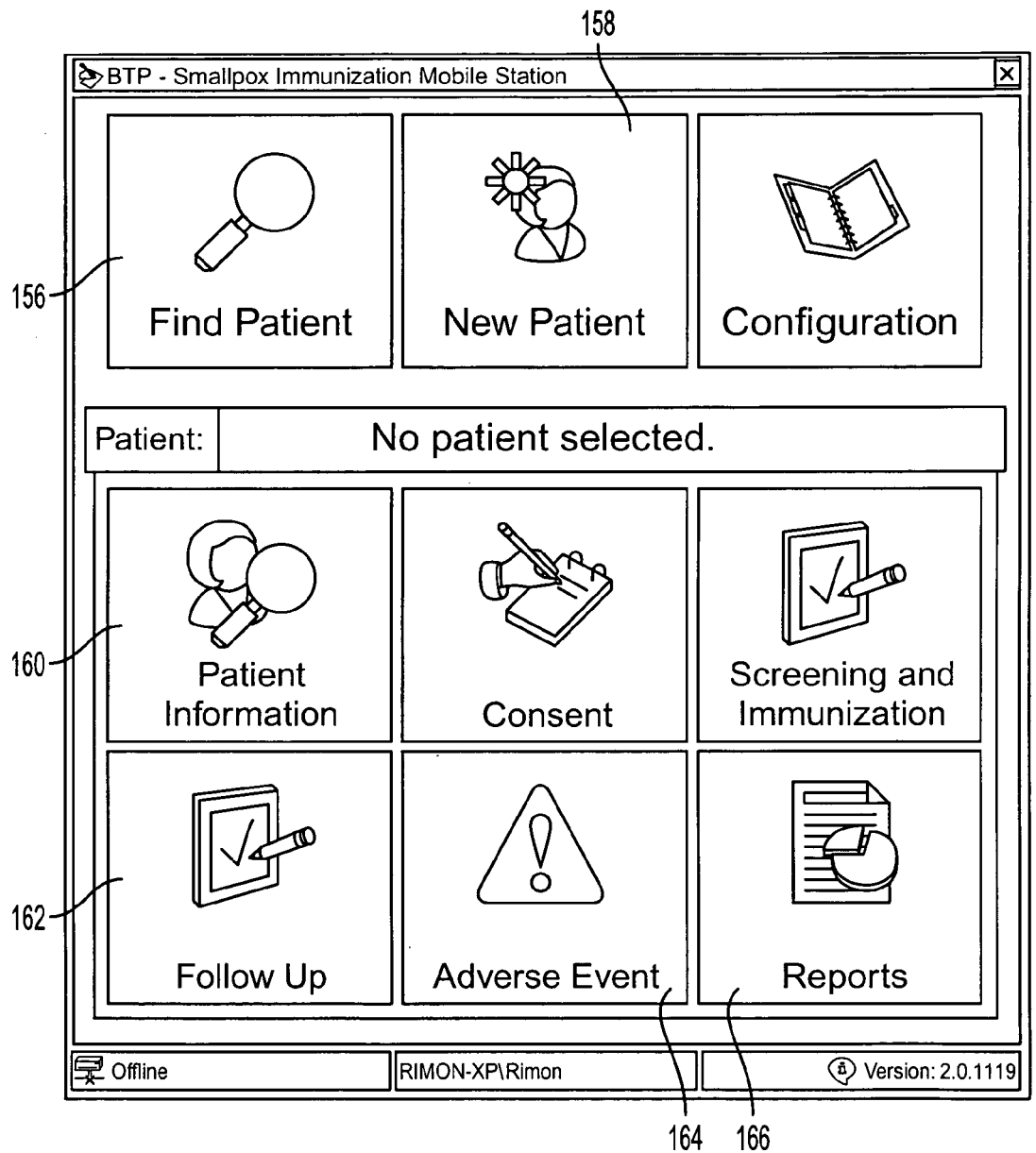
Figure 10:

With continued reference to the exemplary application screen in FIG. 7, Follow Up menu item 162 displays a follow-up form that allows the user to enter follow-up information about a patient, including medical information regarding the vaccination given, record additional pictures, and enter details about physical exams given.

Adverse Events

Clicking an Adverse Events Menu item 164 displays an Adverse Events form that allows the user to enter adverse events information that happened to the patient.

Administration

Clicking an Administration Menu item (not shown) displays an administration tab that allows the user to define and change a list of items.

Reports/Queries

Clicking on the Reports/Queries Menu item 166 displays a list of reports that can be printed for the selected patient and a list of available queries.

Action Form

This is the sub-window within the application that will open after the user clicks on any of the Top Level menu items. The action sub-window contains input and output displays.

Depending on the menu item option the user selected, the look and feel of the action form (e.g., FIGS. 8 through 29) can be slightly different. In general, the action form has a few tabs. Each tab has its own title and enables the user to complete a data entry section in a logical way.

The action form follows, in most cases, the following rules:
has a save button
has a cancel button
has a view patient log button
If there are multiple tabs, arrow buttons on the bottom of the form are provided to allow the user to move between the tabs in a logical order.
The form title will read the name of the menu item the user clicked on.
The top most part of the form reads again the name of the menu item the user clicked on and appends a dash and the patient name.
There is only one action form subwindow open at a time; preferably fills the available space in the application window under the top level menu items.
Bottom Status Bar
The status bar is preferably an indication for the following items:
Patient Information (e.g., First Name, Middle Initials and Last Name)
System Mode (e.g. Stand Alone, Group or Full Network Mode)
Application Version.

Users Actions

This section describes the action available for the users, and the order in which the system allows the actions to occur.

Search/Open

This is one of two options available to the user in the top frame menu items upon launching the application. Clicking on the "Search/Open" menu item brings up a search form (FIG. 8). The search form allows the IMS 80 user to search for existing patients in the system. The user is able to search for existing patients using the following criteria fields:
First Name
Middle Initials
Last Name
Vaccination Date
Immunization system internal identifier
Biometric Information (if entered)
Social Security Number (if entered)

As shown in FIG. 8, when the user clicks on the Search button 170 and the IMS 80 is connected to the data center 82, the system 10 searches in the database 122 at the data center 82 for matching patients. The system 10 can find 0 to n matching patients and displays them in the result grid. The information displayed in the result grid is:
First Name
Middle initials
Last Name
Vaccination Date
Immunization system internal identifier
Social Security Number (Optional)

In all of the alphabetic fields, the IMS 80 application, by default, appends an asterisk to the end of the field. For example, if the user types 'a' in the first name field, the application retrieves all the patients whose first name begins with an 'a'. The asterisk field is not displayed on the form.

The application limits the number of results to a pre-defined value (configured by authorized personnel), with the default being 200. If more then 200 patients answer the search criteria, the application will notify the user and advise to add more search criteria.

The user can then either double-click on a row in the result grid or select a row and click on the Select Patient button. The system 10 then closes the form and changes the status bar to display the selected patient information.

If the system 10 cannot match any patient to the search criteria, it displays a Yes/No message box saying "No Patient Found—Create new patient?" If the user chooses "No", he is returned to the search form that remains pre-populated from the previous search. If the user chooses "Yes", the IMS application closes the Search/Open form and takes the user to the New Patient form, which is preferably pre-populated with the information the user searched for (excluding the vaccination date).

The application does not allow for a search if all of the search criteria fields are empty, and displays an error message if this is the case. In addition to the Search and Open buttons, the IMS generates a screen with a Clear button that will clear all of the fields from the form if detected.

If a biometric device is connected to the Tablet PC, the application displays an additional button that allows the user to search for a patient using his/her fingerprint.

New Patient

Choosing the New Patient menu item 158 changes the application status bar 154 to read "New Patient". It closes the current open patient record (if a patient record was open). A New Patient form (FIG. 9) opens and allows the user to enter the patient information. The available fields are (mandatory fields are specified), but are not limited to:
First Name—Textbox—Mandatory
Middle Initials—Textbox
Last Name—Textbox—Mandatory
Social Security Number (Optional)—Textbox
Date of Birth—Textbox
Gender (radio button)—Mandatory
Ethnicity (combo box)
Home Phone—Textbox
Work Phone—Textbox
Cell Phone—Textbox
Fax Number—Textbox
Email—Textbox
Home Address—Textbox
City—Textbox
State (combo box)
Zip Code—Textbox The Ethnicity and State fields are pre-populated with values. The default value for the state is predefined in the database 82 or local database 80 or 140. The form also has Save, Cancel and Save & Print buttons. When clicking on the Save button, the application checks if all the mandatory fields have values. If one or more fields are missing, the system displays an error message and returns to the form; otherwise, it closes the form. The Save & Print button performs the same tests as the save button but also causes printing of a patient card. The user can also click on the Cancel button, in which case the form closes and the status bar reads "No Patient".

The IMS application might have an optional biometric device that enables a user to record the patient fingerprint. If such a device is enabled, the application allows the user to record the patient's fingerprint. The fingerprint is stored in the database 80 or 140 and eventually the data center 82, and is used as another field to search for the patient records.

Consent

After opening a current patient record or creating a new patient record, the IMS 80 application allows the user to click on the Consent menu item to open a new action form displaying a consent form (e.g., FIGS. 10 and 11) that has a place for four signatures:

Patient's signature

Signature of person conducting informed consent discussion

Signature of investigator or approved designee

Witness to consent procedure (optional signature)

Next to each of the signature boxes, the following buttons are available:

Sign—to enable the signature box

Save—to save the signature

Clear—to clear the current signature

If no signature is stored in the database 80 or 140 and eventually 82, the patient signs in the designated signature box. The patient can sign on the screen of the Tablet PC 80. The digital signature is then stored in the database as an image. At the bottom of the consent screen are Print and Cancel buttons. The Print button initiates printing of the consent form when selected, including the signatures at the appropriate positions. The Cancel button closes the form. The system 10 does not allow for any other menu item to be available until the patient signed on the consent form.

Enrollment and Vaccination

After signing the consent form, the IMS 80 application enables the Enrollment menu item. By clicking the Enrollment menu item, the user obtains a new action form that has multiple tabs. Each tab represents a different part in the vaccination process. In addition, the Enrollment action form allows taking pictures of the vaccinated area of the patient and storing the pictures in the database 80 or 140 and eventually 82, as well as uploading of external files. The user can save his work at any stage by clicking the Save button. The Cancel button closes the form. The next few sections describe the tabs available on the enrollment form.

Medical History

Selecting the Medical history tab displays general questions about the patient medical history. Each question can be answered both for the patient and for a household. The questions are displayed in a grid. Each row in the grid has four cells:

The question

Patient cell—each cell with 2 checkboxes, Yes and No

Household cell—each cell with 2 checkboxes, Yes and No

Additional information—a form-free text area where the user can type.

Some of the questions might require the user to enter additional form-free text in a designated area. In these questions, the IMS application indicates to the user what type of information needs to be provided.

The following table contains exemplary questions:

| Question | Remarks |
| --- | --- |
| Heart disease | |
| Stroke | |
| Seizure | |
| Asthma/emphysema | |
| Cancer /leukemia | If Yes, need to specify what type, when it was diagnosed and how it was treated. |
| Eczema | If Yes, the user has to enter in the free text box if it's active or "history of" and for what period of time |
| Other chronic skin condition | If Yes, needs to specify what type, when it was diagnosed and how it was treated. |

-continued

| Question | Remarks |
| --- | --- |
| Acquired Immune deficiency (HIV) | |
| Autoimmune disorder (ex: lupus) | If Yes, needs to specify what type, when it was diagnosed and how it was treated. |
| Hepatitis | |
| Frequent/recurrent/severe infections | If Yes, needs to specify what type, when it was diagnosed and how it was treated. |
| Other | If Yes, needs to describe |

Additional questions might be added to this grid.

Current Medications

After selecting in the current medication tab (FIG. 12), the user is provided with a screen (FIG. 13) to enter information about any medication currently being taken. In order to enter information in the grid, the user will first have to check a "Yes" checkbox in response to query "Is the patient currently taking any medications (prescription and/or over the counter) ". The form has a grid with 4 columns:

Medication name

Medication dosage

Start Date

Reason for taking

The screen in FIG. 13 has text boxes with the above titles as the grid columns in which a user enters the information. The lines are displayed in the order they were entered. The user is able to click on a line and choose to delete it. The entry fields for medication names and dosage fields are pre-populated lists. The pre-populated lists include the value "Other". If the user selects "Other", the user can enter data in an associated text box.

Vaccination History

Selecting the vaccination history tab (FIG. 12) causes the IMS 80 application to generate an Immunization History screen (FIG. 14) that preferably consists of three parts:

Previous Vaccination for Smallpox

This is a Yes/No question. If the user chooses the "Yes" checkbox, a textbox for entering additional information such as when/where is be enabled. The text box allows for entry of the following information:

Vaccination date (if known)—text box

What was your age range?—pull-down menu (0-5; 6-10; 11-15; 16-20; 21-30; 31-40; 41-50; 51-55; 56-60; 61-65; 66-)

Was it in childhood?—Y/N

Was it in military service?—Y/N

Lot number (if known)—text box

Location—combo box

Number of doses—text box

Was the information based on recall or document?—R/D

Remarks—text box

Take Response—check one of the following: Normal; No Take; Scar; Adverse Event; Equivocal)

Vaccinations Received in the Last 30 Days

Figure 14:

The screen in FIG. 14 also has a Yes/No questions reading "Other vaccinations in the past 30 days?." If the user checks the "Yes" box, a grid is enabled which has the following columns:

Vaccination date—text box

Vaccination type—combo box

Lot number—text box

Location—combo box

Number of doses—text box
Remarks—text box
Serious Reaction to Vaccination in the Past The screen in FIG. 14 also has a checkbox question reading "Have you ever had a serious reaction after any vaccination?." If the user checks the "Yes" option, a grid is enabled that allows the user to enter the following information:
Description—text box
Age—text box
Vaccination—combo box
Reaction after dose number—text box
Women Only The women only tab can be enabled if the patient is a woman. The first portion of the tab preferably shows the following question: "Date of last menstrual period?" Below, there is a grid with a set of yes/no questions and a cell for remarks. The following questions are exemplary:

| Question | Remarks |
| --- | --- |
| Are you currently pregnant? | |
| Are you currently Breastfeeding? | |
| Currently using birth control? | If yes the user will need to provide the name in the remarks area. |

Additional questions might be added to this grid.
Approval

Figure 15:
Figure 16:
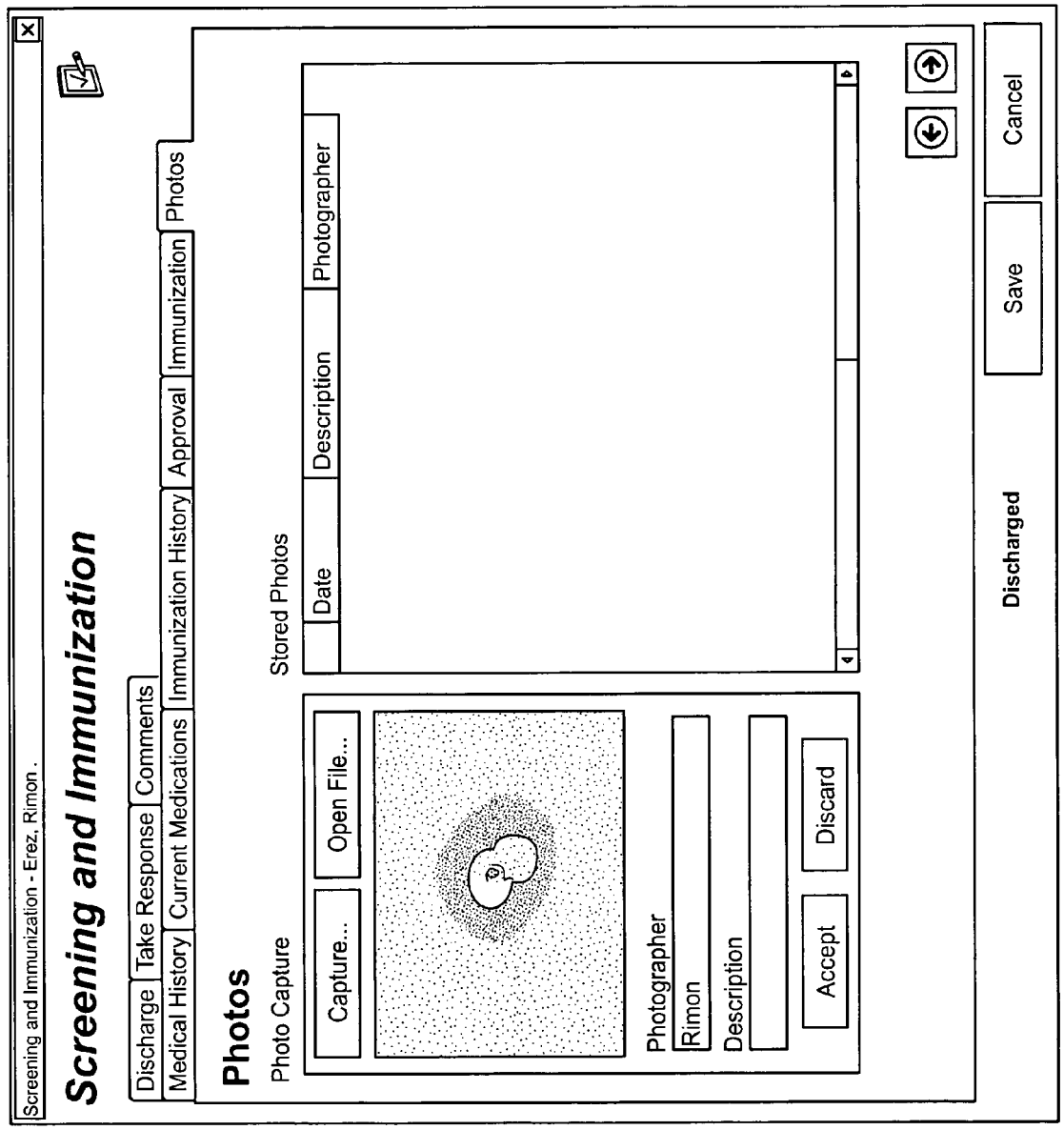

Selecting the Approval tab causes the IMS 80 application to generate a screen such as the one in FIG. 15 that displays all of the information defined in the application as essential for the physician to give the vaccination. This screen aggregates this information into one form and allows a physician to review it before proceeding with the vaccination process. The information displayed in this tab can be configurable.
Immunization The Approval screen (FIG. 15) can provide a signature box for obtaining a digital signature for storage. Alternatively, a separate Immunization screen (not shown) can be provided to allow the user to enter the following information
Date of vaccination—text box
Vaccination lot number—text box
Vaccination site—combo box
Vaccinator name—text box
Signature box—digital signature box
Sign button The vaccinator name field will be pre-populated with the name of the user who is signed in to the Tablet PC, but the user can override it.
Photos If the Photos tab in the screen depicted in FIG. 12 is selected, a screen as shown in FIG. 16 is provided to allow the user to capture photos of the patient vaccinated area. The screen preferably consists of two areas:
Photo Capture
This area allows the user to capture a photo using a digital camera attached (or connected via Wi-Fi) to the IMS 80 or load a photo from a file. Once the pictures are captured, the user can add a description to the photo and to click on the "Accept Photo" button to add the captured picture to the Stored Photos. If he chooses not to save the photo, the user can click again on the "Capture Photo" button to capture a new photo.
Stored Photos
This area displays the captured photo(s) for the patient and the description. The user can double click on a picture to open in a new window. The user will then be able to zoom in/out from the picture.

Figure 17:
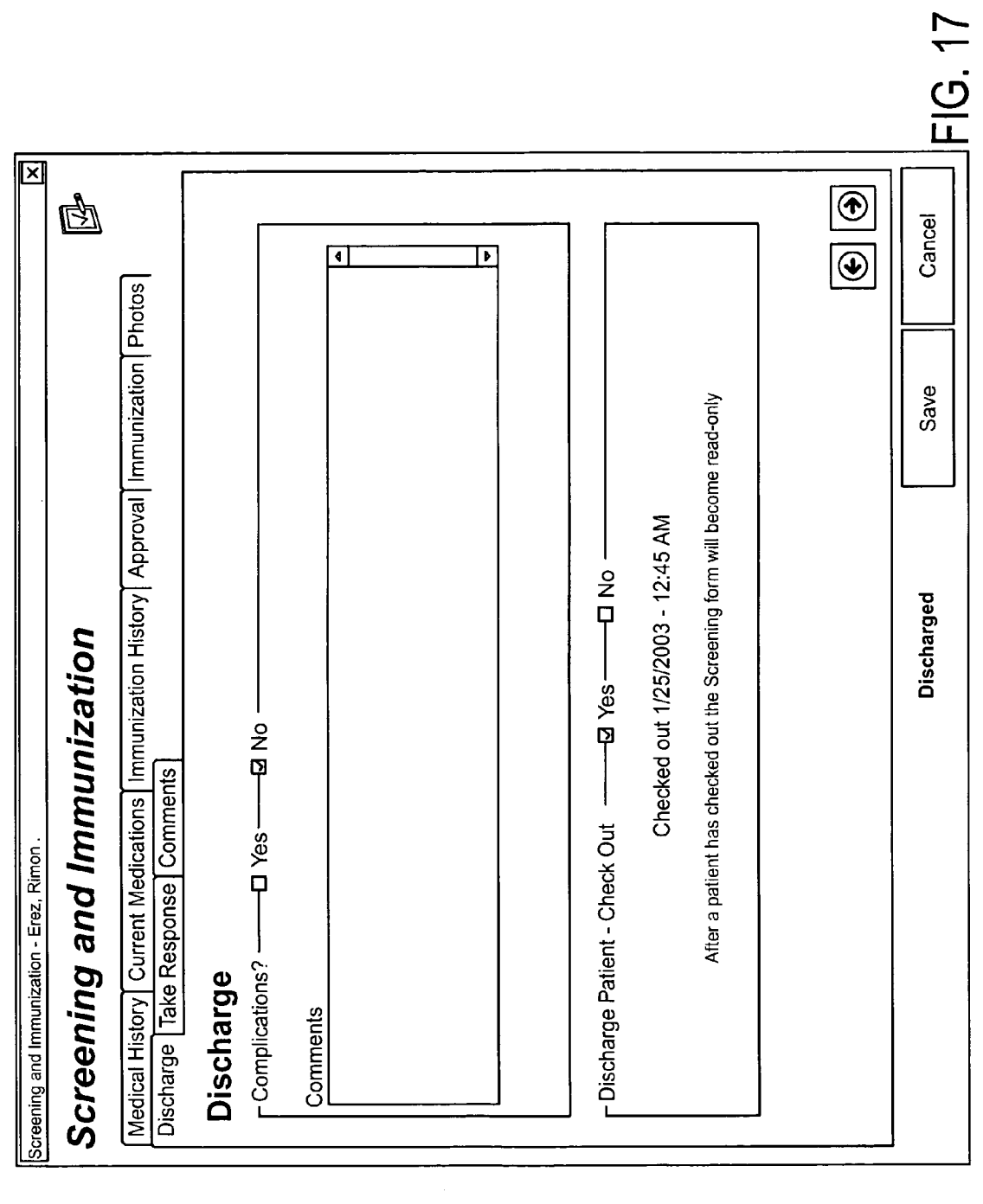
Figure 18:
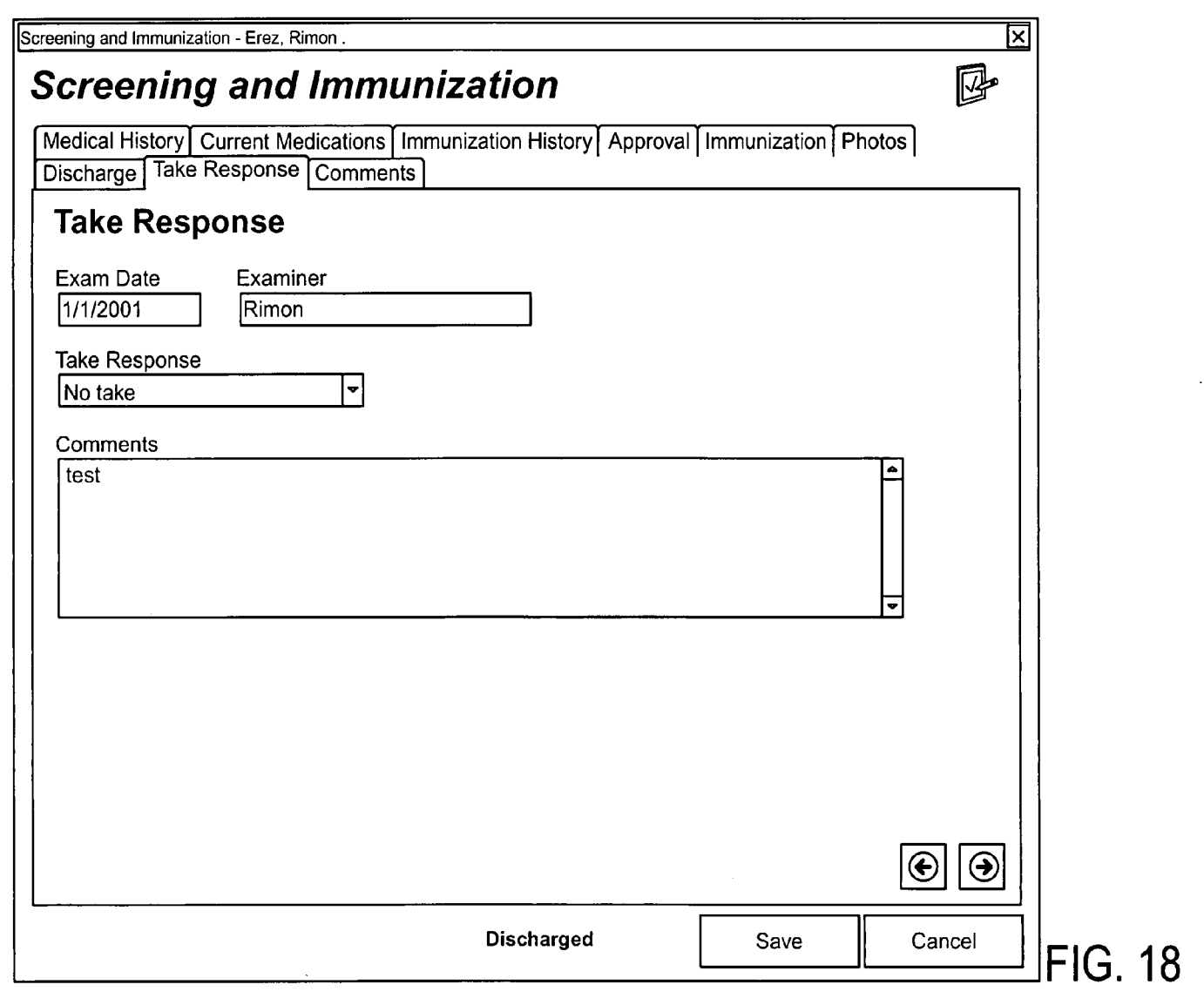
Figure 19:
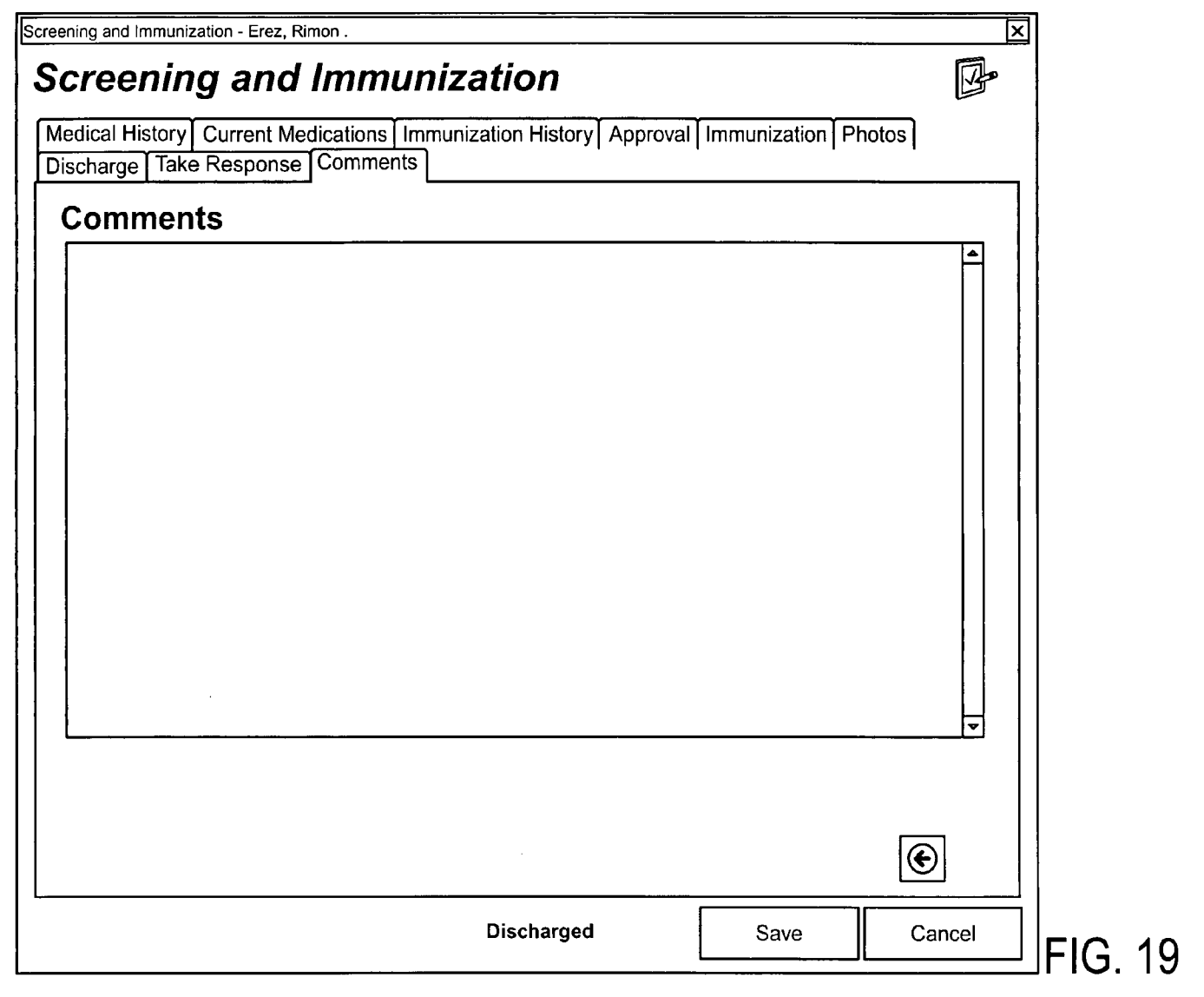
Figure 20:
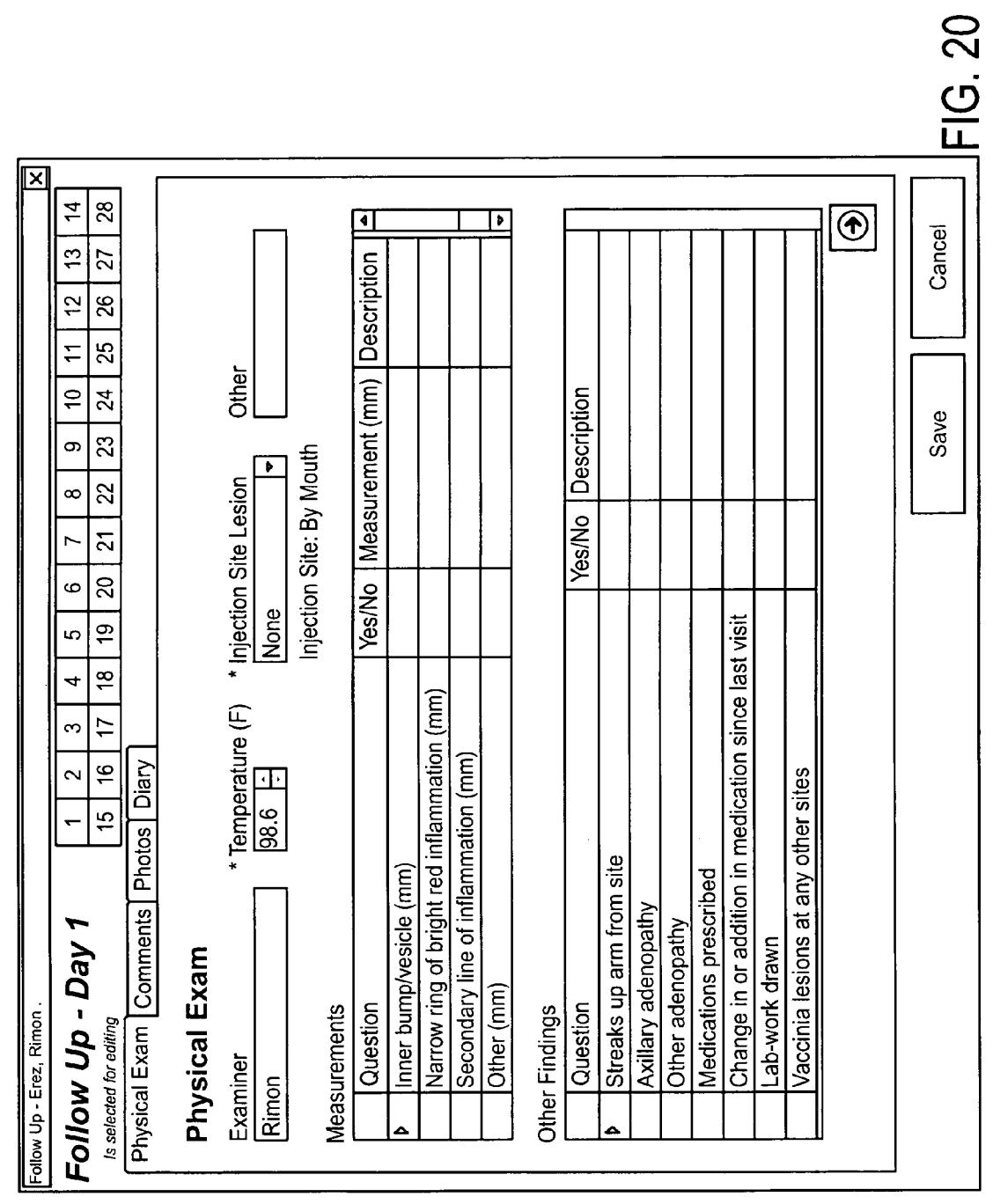

A field is provided that the clinician, who is monitoring the picture taking, can use to fill in his/her name. The name field is pre-populated with the username logged in to the Tablet PC, but can be overridden by the user. Other screens can be generated by the IMS 80 application to allow a user to enter information regarding patient discharge, take response, and comments, as shown in FIGS. 17, 18 and 19, respectively.
Follow Up After the enrollment process is completed, the IMS 80 application can enable the Follow-Up menu item (FIG. 7). The form, as shown in FIG. 20, enables the user to enter follow-up information up to 28 days. The user will have at the top of the action form a series of numbers from 1 to 28, each number representing a day. The user can click on one of the days and enter the information regarding the selected day. Clicking a day changes the title of the form to read the selected day, in addition to the other information. The form has Save and Cancel buttons. The forms can be filled by a clinician (e.g., in case of an Office visit, or a phone call to or from the patient). The patient can also complete the form over the internet using a web browser.
Diary By selecting this tab, the IMS 80 application generates a screen as shown in FIG. 21 that allows the user to specify if any symptom has occurred for that specific day. The screen has a grid with 3 columns in it as follows:
Symptom/Question
Yes/No check box (or a numeric value)
Additional information—a free text area where the user can type.

Figure 22:
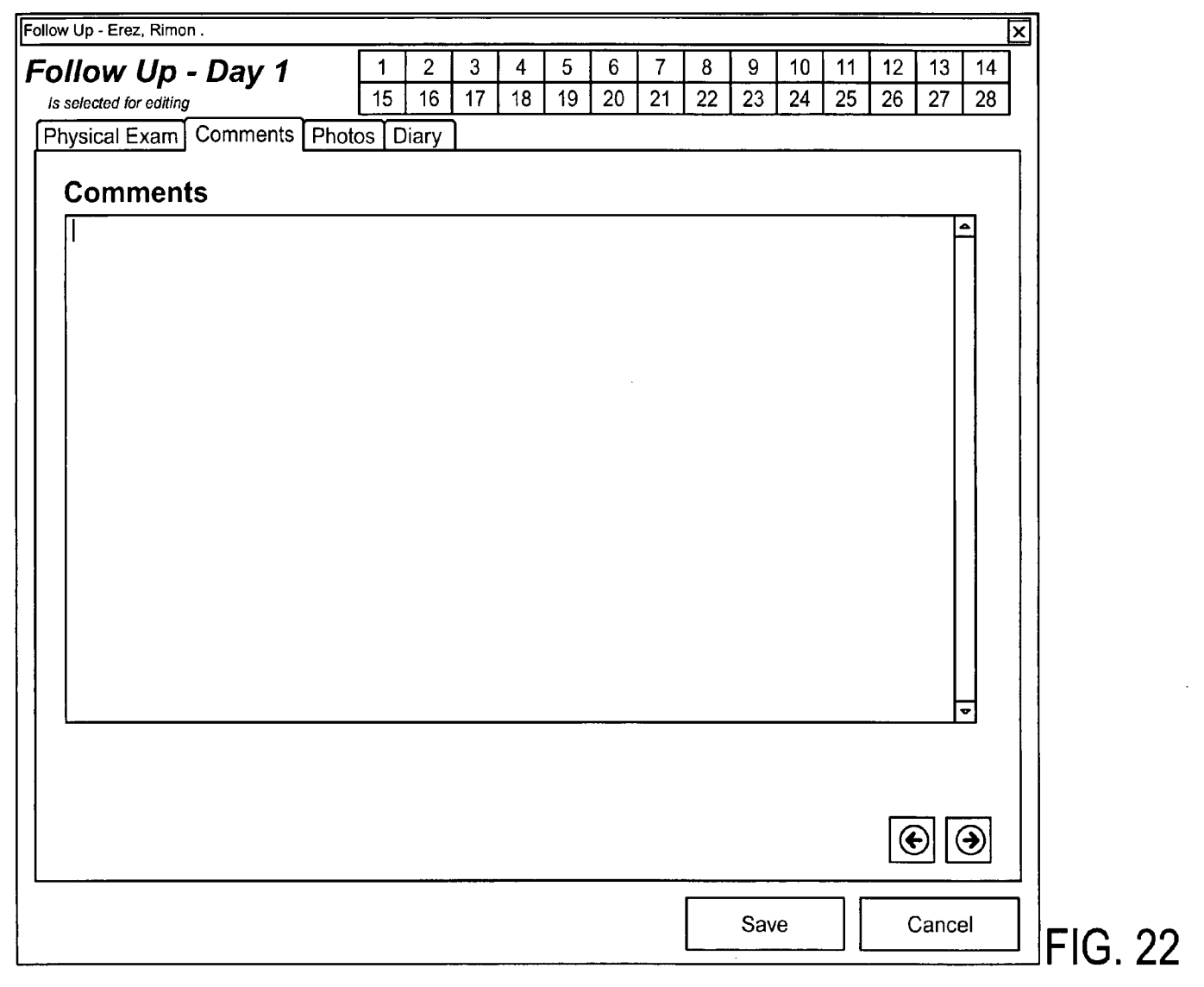

Some of the questions require the user to enter additional form-free text in a designated area. For these questions, the application indicates to the user what type of information he needs to supply. Also, a free-text area can be provided on another screen, as shown in FIG. 22.

The form can have a Print Username & Password button that prints a unique username and password for the patient There can be a web form on the internet that allows patients to fill the diary form from any standard web-browser.

The following table contains an exemplary the list of symptoms/questions displayed in the grid.

| Symptom/Question | Remarks |
| --- | --- |
| Scab fell off today? | |
| No Symptoms | |
| Temperature | |
| Fever | |
| Chills | |
| Joint pain | |
| Muscle pain | |
| Fatigue | |
| Loss of Appetite | |
| Cough | |
| Swelling/tender lymph nodes | |
| Itching on body | |
| Headache | |
| Backache | |
| Symptoms at Lesion Site: | |
| Pimple | |
| Vesicle (blister) | |
| Ulcer | |
| Scab | |
| Redness | |

-continued

| Symptom/Question | Remarks |
|---|---|
| Swelling | |
| Warmth | |
| Itching | |
| Pain | If value exceeds 0, a description will be required. |
| Key: 0 = no pain | |
| 1 = painful to touch | |
| 2 = pain when arm is moved | |
| 3 = pain all the time | |
| Streaks on arm | |
| Vaccinia-type lesion NOT at site of vaccination | In case the user selects this symptom, the application will indicate a description and location are required in the additional information cell. |
| Non-Vaccinia type rashes | In case the user selects this symptom, the application will indicate a description and location are required in the additional information cell. |
| Any new prescription medication taken? | If Yes, a description will be required. |
| Was Medical care sought today? | If yes, the following questions will appear: Provider's Last Name Provider's First Name Provider's Address Provider's Phone Permission to acquire medical records - Y/N |

If medical care was sought, and a permission to acquire the medical records was given by the patient, a signature box will appear on the screen to request the patient's signature. If the diary (i.e., FIG. 21) was filled without the patient being in the presence of a user and his/her Tablet PC 80, (e.g., by using the web application), a message indicates a diary card needs to be signed and sent to the clinic in order to acquire the medical records.

Additional questions might be added to the grid depicted in FIG. 21. For example, data ranges can be defined for each of the numeric questions so that the user can be alerted of abnormalities (e.g., a temperature above the average for patients on day 3). The text for the alert can be defined by a user with administrative rights. The alert could, for example, indicate that a referral to a clinician is recommended.

Photos

Figure 23:
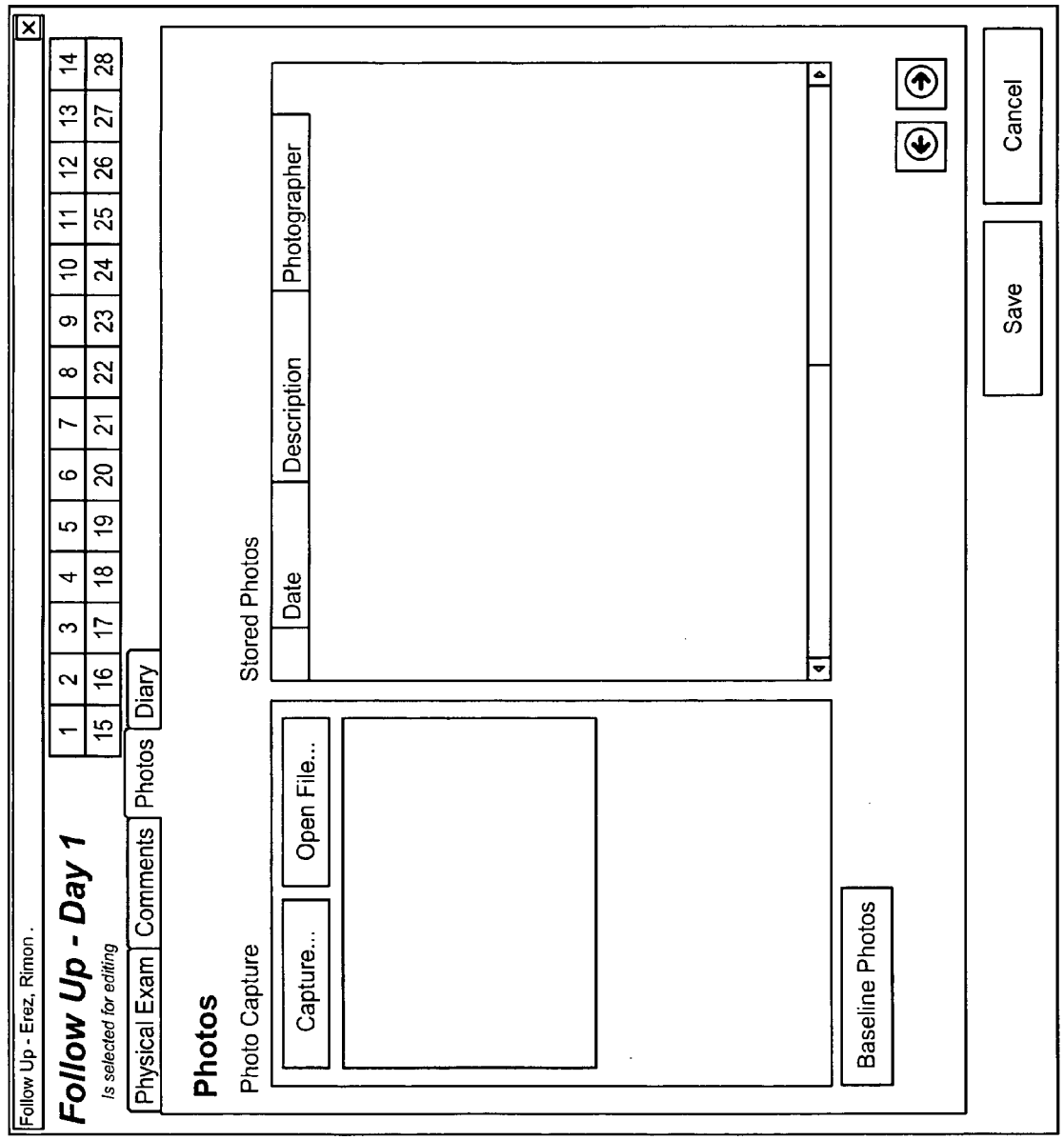
Figure 27:

If the Photos tab on the Follow-Up screen (e.g., FIG. 20) is selected, a screen such as that depicted in FIG. 23 is provided to the user to allow capture of photos of the patient's skin, in each one of the diary dates. The screen can consist of two areas:

Photo Capture
This area allows to the user capture a photo using a digital camera attached to the IMS 80, or to load a photo from a file. Once the picture is captured, the user can add a description to the photo and click on an "Add Photo" button to add the captured picture to the Stored Photos at the IMS or local server 140 and eventually at the data center 82. If the user chooses not to save the photo, he can click again on the "Capture Photo" button to capture a new photo.

Stored Photos
This area displays the captured photo for the patient and its description. The user can double click on a picture and open in a new window to zoom in/out from the picture.

Physical Exam

With continued reference to FIG. 20, the Physical Exam form allows the user to enter information regarding a physical exam conducted with the patient. The examiner can select his/her name from a pre-populated list, and sign the form once completed.

The user can enter the following exemplary information:

| Symptom/Question | Remarks |
|---|---|
| Inner bump/vesicle (mm) | |
| Narrow ring of bright red inflammation (mm) | |
| Secondary line of inflammation (mm) | |
| Other (mm) | In case the question is answered, the user will have to provide a description |
| Streaks up arm from site | Yes/No question. In case Yes is selected, the user will have to provide a description |
| Axillary adenopathy | Yes/No question. In case Yes is selected, the user will have to provide measurements and descriptions |
| Other adenopathy | Yes/No question. In case Yes is selected, the user will have to provide a description |
| Vaccinia lesions at any other sites | Yes/No question, In case Yes is selected, the user will have to provide a description |
| Medications prescribed | Yes/No question. If Yes, listing is required |
| Change in or addition in medication since last visit | |
| Lab-work drawn | Yes/No question. If No, give reason |

If the comments tab is selected, the user can use the free text box in FIG. 22 to add comments about the current day.

Adverse Events

Once the enrollment and vaccination process has been completed, the IMS 80 application can enable the Adverse Events menu item, as shown in FIG. 24. This form has Save, Cancel and Print Report buttons. The print report prints an adverse event report in the format of the CDC's VAERS report using the information entered via the IMS 80 application.

Event Details

The top of the screen in FIG. 24 has a field that requests entry of the date of onset, and a text box for the event details. A list of categories appears below, but additional possible categories could be added. For each category, a Y/N check box appears and, if checked, additional information is required. For example, the screen in FIG. 24 can request the following information:

| Category (check one or more) | Remarks |
|---|---|
| Patient died/date patient died | If the checkbox is selected the user will have to enter the date of death. |
| Life threatening illness | |
| Resulted in significant disability | |
| Resulted in permanent disability | |
| Laboratory Toxicity | |
| Assessed as serious by the Clinician | |
| Prolongation of hospitalization | |
| Congenital Anomaly | |
| Required hospitalization and number of days of hospitalization | If the checkbox is selected the user will have to enter the number of days in the other column. |

| Category (check one or more) | Remarks |
| --- | --- |
| Others | If the checkbox is selected, the user will be required to provide a description |
| Subject Status/Outcome: | |
| Ongoing | |
| Resolved without sequelae | If checked, date of resolution is required |
| Resolved with sequelae | If checked, description and the date of resolution are required. |
| Severity (Mark one) | |
| Mild | |
| Moderate | |
| Severe | |
| Life-threatening | |
| Death | |

Vaccinations and Medication

Figure 25:
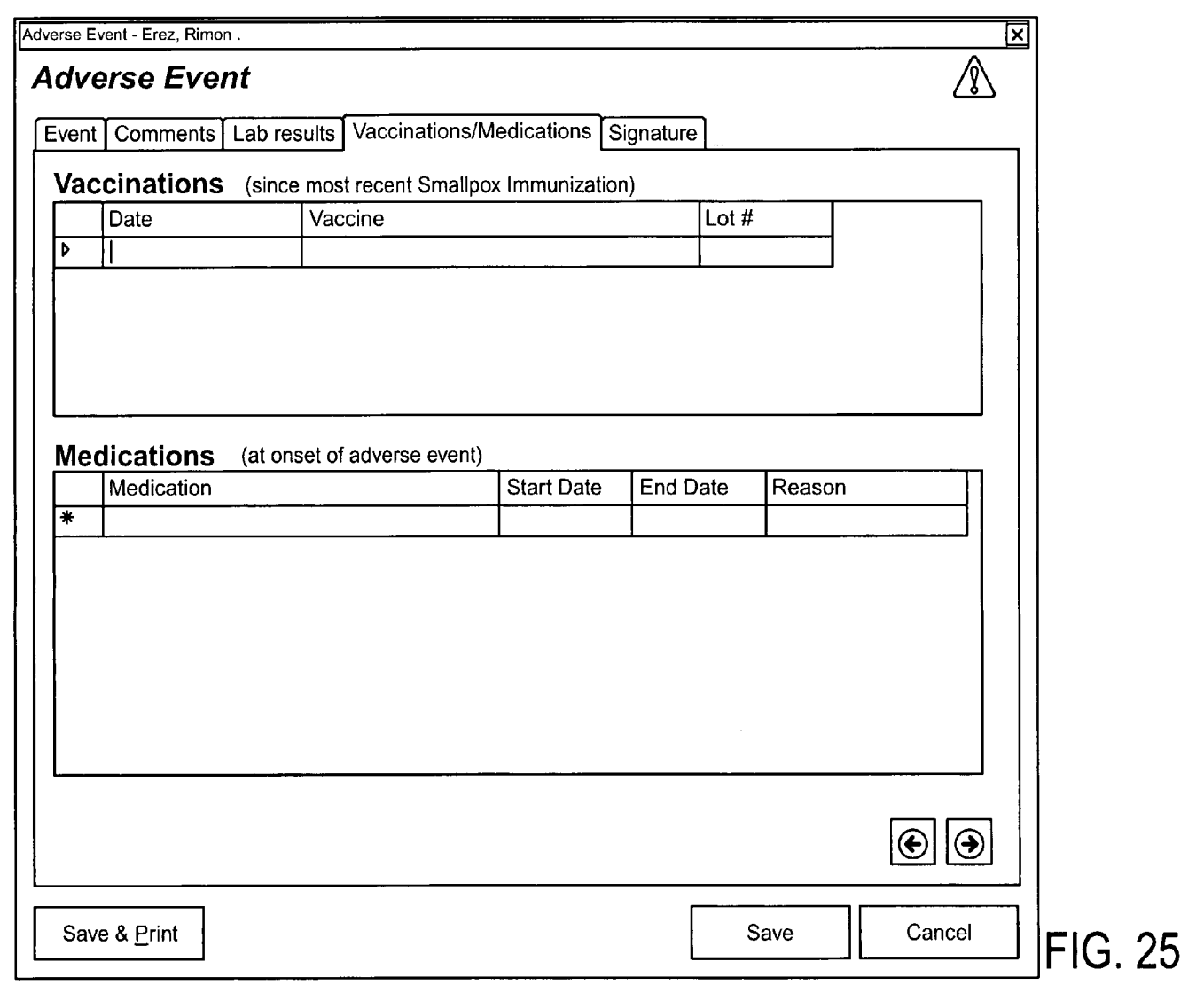

This tab on the Adverse Event screen (FIG. 24) allows the user to enter information about vaccinations the patient received since he got the current vaccination, as well as medication given after the smallpox vaccination, on a form such as that depicted in FIG. 25.

The vaccination area has two fields:
Vaccination Name—Pull-down menu of possible vaccinations
Vaccination Date—Textbox
The medication area has the following fields:
Medication Name—Pull-down menu of possible vaccinations
Medication Start Date—Textbox
Medication End Date—Textbox
Reason Next to these fields an Add button can be provided. The user can enter the information and click on the Add button to add the information to a grid that is positioned below the above fields, for example.

Lab Work

Figure 26:
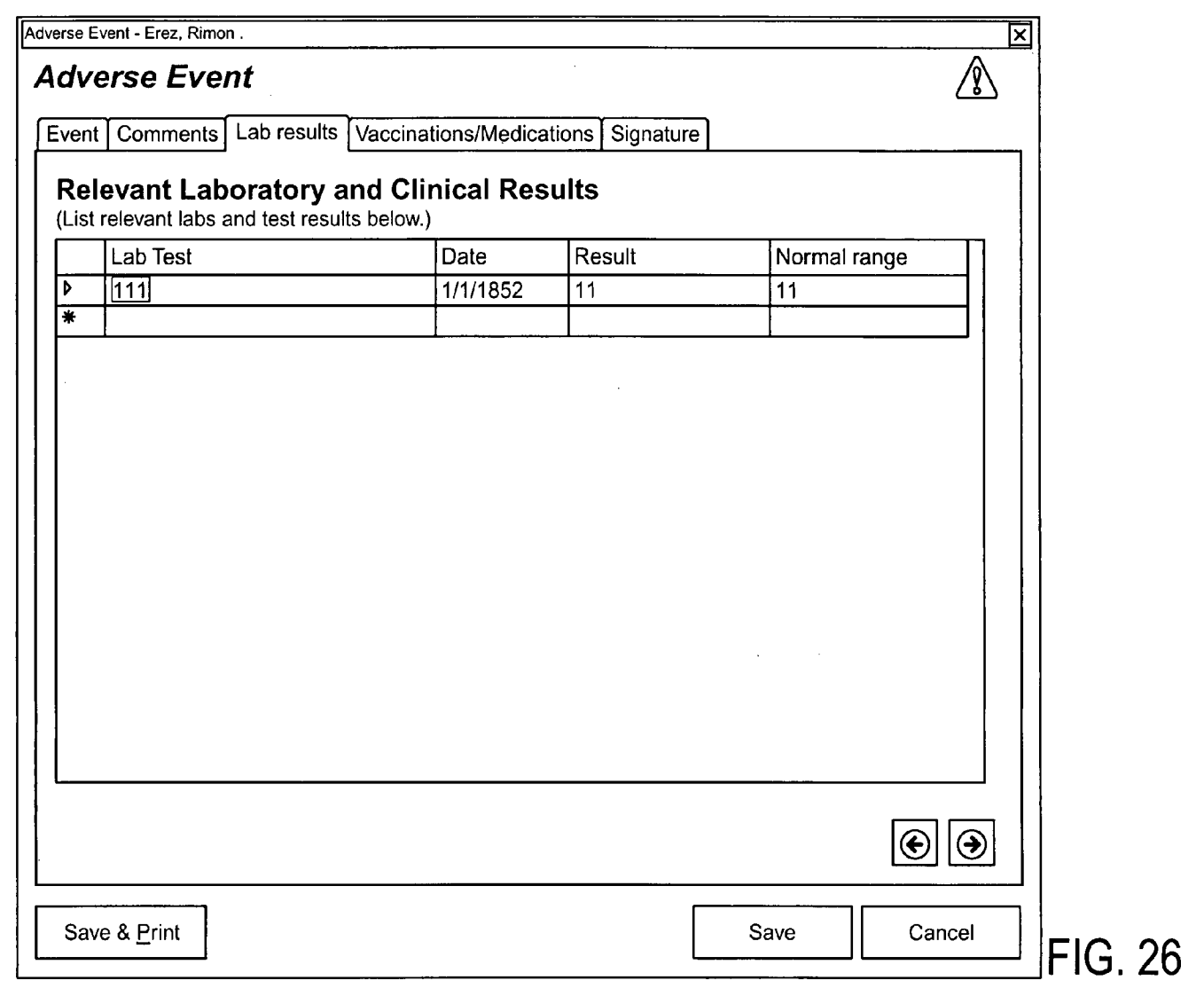

Selecting the Lab Work tab causes the IMS 80 application to generate a screen such as that depicted in FIG. 26 to allow the user to enter or upload from external sources information about lab work done for the patient. For each lab test, the collection date and results will be entered, along with the normal range for the test. A column indicating an abnormal result (meaning a result not within the normal range) will flag automatically a check mark.

Signature

A screen (FIG. 27) can be generated by the IMS 80 application in response to selection of the signature tab which has place for two signatures, that is, one for the person who completed the form and one for the investigator. In addition to the signature boxes, a text box is provided next to each signature box that is pre-populated with the username who is logged in to the Tablet PC. The application allows the user to override this name. In addition to these fields, there are two more fields to indicate the date the report was submitted to the IRB and to the FDA, respectively.

Administration

The following section describes different administrative screens that can be generated by the IMS 80 application.

Clinic Information

This screen (not shown) allows the user to identify the clinic in which they are working. The user may select the clinic by name or clinic ID. When a clinic is selected the clinic name, ID, address, and phone number is displayed.

Reports

Data resides in the clinics (e.g., of the IMSs 80 and optionally at a local server 140) and the data center 82. Reports run by the Tablet PC against the data at the clinic will have access to that clinic's data only. Reports run by a separate web application against the data center 82 will have access to data for all clinics in a state, but access to any specific user is based on the access rights of that user.

Clinic Reports

Each Tablet PC 80 application has the ability to run reports regarding the clinic to which it is connected. The reports can be pre-defined and allow the users to retrieve information they need about the patients and immunization process within the clinic. The reports can be divided into the following types:
Patient Specific Reports
Clinic Specific Reports
Patient Specific Reports These reports print information about a specific patient. The user will be able to print them as part of the immunization process by clicking on the Print button in a specific form, or by going to a designated reports area and choosing a report to print. Each report will have a default number of copies to be printed, but could be configured by the user. The following table contains the list of available reports. Additional reports could be added.

| Report Name | Description |
| --- | --- |
| Patient Card | The patient card will have all the information about the patient as entered into the system |
| Consent Form | This is the consent form printed with the patient signature on it. |
| Vaccine Adverse Event Report | The pre-defined CDC report. |
| Patient Web Site Account Information | Information for the patient to use to gain access to the web-based application. Must include patient name, user ID, and password. |

Clinic Specific Reports

These reports present information held at the local clinic for one or more patients. The reports are predefined. The report results can be filtered using predefined parameters. The following table contains the list of potential reports. Additional reports can be added.

| Report Name | Description |
| --- | --- |
| CDC Vaccinia IND Roster | A daily listing of activity, to be sent to CDC. To be run by a user. |
| Patients Cards | Up to full patient cards. |
| Vaccine Adverse Events Summary | |
| Patients Web Site Account Information | |

Where applicable, the result is a list of all patients that fit these criteria, and by clicking on a specific patient name, the IMS 80 application will open the record. The user also has the option to print a list with these patients' information.

Data Center Reports

A web-based reporting application allows the user to run predefined reports on data for all clinics in a state. Report results can be filtered using predefined parameters. The authorized user has the ability to view information regarding one or more patients or one or more clinics. The reporting application controls the reports and parameter values available by user group. The following exemplary users groups have been identified:

Selected clinic personnel
  Selected state personnel
  Selected national personnel
  Selected call center and system administration personnel Members of the selected clinic personnel group will preferably only be able to see data on particular patients from their clinic, unless the user has access-rights to information regarding other patients.

The following table lists reports that are representative of reports available from the data center 82.

| Report Name/Type | Description |
|---|---|
| Comparisons Reports | These reports will allow the user to compare between 2 or more clinics, or between a clinic and the average of all other clinics on a set of various parameters, such as: number of vaccination given per day Progress pace - the user will be able to define a comparison unit (hour, day, week etc.) and to see the progress pace for a specific clinic and the comparisons between 2 or more clinics. The reports will be available both in absolute number and in a graphic display. |
| Patient Reports | These reports will display all the information available in the system for a group of patients. |
| Data Reports | These reports will allow the user to analyze the information stored in the database, based on various parameters and criteria. For example, the user will be able to see a report that will display in a graph form the average size of the lesion on day 5, where each data point represents the average in a clinic. Such reports will be available for each numeric data stored in the database. The user will have the ability to compare the values to the overall values and to see abnormalities in groups of patients/clinics. |

Global Administration

An administrator at the data center 82 can perform the following tasks:

add, delete, and change users
  change username password
  disable existing users
  add new clinic
  distribute new software versions
  distribute changes to the database schema These operations are preferably done by an authorized user with access to the entire database 122 and can be pushed to each clinic connected to the interne. FIGS. 28 and 29 illustrate exemplary administration screens generated, for example, at the IMS 80 or the data center 82 to configure IMS 80 application settings.

Web Access to Patient Diary

During the enrollment and vaccination process, each patient receives at the clinic a user ID and a password. The user ID can be the clinic ID and an internal user ID which the application auto naturally generates, and a password (e.g., automatically generated by the system 10) for each patient.

In order to allow a patient to enter his/her diary report via a web-browser, the system provides a web application that enables patients to login and enter the information. Each patient is able to login to a designated website using the username and password received. Following authentication, he has access to the diary cards as defined above. The information is recorded at the data center 82 and synchronized with the associated clinic.

It should be understood the processes described are only exemplary and any suitable permutation of the processes may be used. The foregoing disclosure and description of the invention is illustrative and explanatory thereof and various changes to the size, shape, materials, components, and order may be made without departing from the spirit of the invention. While the present invention has been described with reference to the disclosed embodiments, it is to be readily apparent to those of ordinary skill in the art that changes and modifications to the form in details may be made without departing from the spirit and scope of the invention.

What is claimed is:

1. A system for managing immunization and disease information comprising:

a computer-readable database that stores disease information, vaccination information, electronic patient records, and vaccine administration data, wherein said disease information and said vaccination information comprise, respectively, information about a vaccine preventable disease and the vaccine therefor;

said database further comprising selected ranges for normal body temperature and size measurements of skin characteristics at a vaccination site for each of a plurality of days following a vaccination;

a patient transaction module configured to:

provide a patient with at least one of said disease information, said vaccination information and his corresponding one of said electronic patient records from said database, receive patient input data from the patient on at least a daily basis after a received vaccination, and store said patient input data in the corresponding one of said electronic patient records in said database, said patent input data comprising adverse reaction data relating to an adverse reaction in the patient from a vaccination, said adverse reaction data comprising measurements of the patient's temperature and size of skin characteristics of a site of said vaccination on the patient's body and digital images of the site of said vaccination taken on each of a plurality of days after the vaccination is administered;

a service provider transaction module configured to:

receive service provider input data and store said service provider input data in corresponding said electronic patient records, wherein said service provider input data comprises biographical patient information, vaccinations administered to corresponding patients, and location of vaccinations administered, said service provider input data further comprising data selected from the group consisting of patient medical history, vaccination date, vaccination lot number, and adverse event data relating to an adverse reaction to a vaccine;

generate said vaccine administration data using said provider input data, and transmit stored data from said database to service providers, relate said measurements and said digital images in said database to the corresponding one of said electronic patient records for said patient, to a recorded vaccination administered by said service provider, and to said selected ranges for each of the plurality of days, and determine when at least one of said measurements is outside the selected range corresponding to a selected one of the plurality of days and generate an alert indicating that referral of the patient to a health provider is recommended.

2. A system as claimed in claim 1, further comprising a customer transaction module for providing said vaccination administration data and said disease information retrieved from the database to a customer upon request, said customer transaction module being configured to analyze said vaccination administration data to identify which of said patients in a selected group have been vaccinated with a selected vaccine, and to analyze said disease information comprising symptoms being experienced by said patients and documented in said electronic patient records for epidemic evaluation and control.

3. A system as claimed in claim 2, wherein said customer is selected from the group consisting of a government, a state government, a national government, a hospital, a health clinic, a call center, a retailer, a pharmacy, a corporation, an employer, a regulatory group, a government agency, and a disease control center.

4. A system as claimed in claim 2, wherein said customer transaction module is configured to analyze said vaccination administration information and determine compliance with regulatory requirements relating to vaccinations.

5. A system as claimed in claim 2, wherein said system is implemented by said customer for bio-terrorism preparedness.

6. A system as claimed in claim 1, wherein locations of vaccination administration data comprises identification data for respective clinics, and clinic-specific information about a selected clinic is retrieved from said vaccination administration data in said database to generate clinic reports regarding vaccinations occurring at the clinic.

7. A system as claimed in claim 6, wherein said clinic-specific information is selected from the group consisting of a Center for Disease Control Vaccinia IND Roster listing clinic activity, said electronic patient records of patients who visited the clinic, and a summary of vaccine adverse events.

8. A system as claimed in claim 6, wherein said clinic-specific information for a plurality of clinics is retrieved from said vaccination administration data in said database to generate reports regarding multiple vaccination administration locations.

9. A system as claimed in claim 1, further comprising at least one remote processing device programmable to collect and store said service provider input data.

10. A system as claimed in claim 9, wherein said remote processing device comprises an application program configured to automatically generate Center for Disease Control Vaccine Adverse Event Reports with data from said electronic patient records and said vaccination administration data.

11. A system as claimed in claim 1, wherein said service provider transaction module is provided in a portable computer located at a clinic corresponding to one of a plurality of temporary and moveable locations of vaccination administration and comprising a global position/mapping module, said computer being operable remotely from said database and selectively synchronized with said database, said service provider transaction module in said computer being configured to process said vaccination administration data comprising tracking data relating to said patients vaccinated at said clinic, and to generate clinic-specific reports comprising data relating to vaccinations administered at said clinic and adverse events reported at said clinic.

12. A system as claimed in claim 11, wherein a plurality of said service provider transaction modules are provided in respective computers at corresponding ones of said plurality of locations of vaccination administration to create a plurality of clinics, and said database is configured to receive and store clinic-specific said vaccination administration data from said computers at respective said plurality of clinics, said clinic-specific vaccination administration data comprising identification of said location of vaccination administration via said global position/mapping module, patient information corresponding to patients receiving vaccinations at said location of vaccination administration, vaccination date, vaccination lot number, and follow-up data relating to a reaction to a vaccine at said location of vaccination administration.

13. A system as claimed in claim 12, further comprising a customer transaction module configured to analyze said clinic-specific vaccination administration data associated with selected ones of said plurality of clinics to determine for each of said selected clinics a clinic average for at least one parameter associated with said follow-up data, and to compare said clinic average with an overall average for said parameter for tracing and analysis of epidemic spread and control via vaccination based on said identification of said location of each of said selected clinics and said average comparisons.

14. A system as claimed in claim 1, wherein said service provider transaction module is implemented in an immunization mobile station and said database is implemented in a data center, said service provider transaction module being further configured to establish at least one ad-hoc network with said data center, operate in a global mode when connected to said data center by transmitting said electronic patient records to said data center for synchronization and storage in said database, operate as a group master in a group mode by communicating with a plurality of other immunization mobile stations via peer-to-peer communication and exchanging information comprising at least said patient data and said vaccination administration data via a second ad-hoc network even when no connectivity to said data center is available, and maintain and synchronized said exchanged information for said plurality of other immunization mobile stations while in said group mode and provide said exchanged information to said data center when connectivity to said data center is available.

15. A system as claimed in claim 14, wherein said service provider transaction module is configured to determine a health risk to the patient for receiving a vaccination based on at least one of said service provider input data and said patient input data, and on said vaccination information in said database, and generate automatically an alert recommending against the patient receiving a vaccination based on said health risk.

16. A system as claimed in claim 1, wherein at least one of said patient transaction module and said service provider transaction module is configured to generate screens to guide a user when entering said adverse reaction data and said adverse event data, respectively, to comply with protocols for documenting adverse events to vaccines.

17. A system as claimed in claim 16, wherein said protocols are set forth by at least one of the Center for Disease Control and the National Institutes of Health.

18. A system as claimed in claim 1, wherein said service provider transaction module is configured to retrieve said digital images for said patient for each of a plurality of days and baseline photos for comparison and generate a notification to a government agency for disease tracking when a lesion captured in one of said digital images is determined to require expert assessment and notification to the government agency.

19. A system as claimed in claim 1, wherein said patient transaction module is configured to store patient input data comprising a digital image of a disease symptom.

20. A system as claimed in claim 1, wherein said disease symptom is a smallpox lesion.

21. A system as claimed in claim 1, wherein said patient transaction module is implemented using at least one of an immunization mobile station that can be connected to said database, and a web browser synchronized with at least one of said immunization mobile station and said database.

* * * * *